(12) United States Patent
Mohr et al.

(10) Patent No.: US 8,706,184 B2
(45) Date of Patent: Apr. 22, 2014

(54) METHODS AND APPARATUS FOR DISPLAYING ENHANCED IMAGING DATA ON A CLINICAL IMAGE

(75) Inventors: Catherine Mohr, Mountain View, CA (US); Ian McDowall, Woodside, CA (US); Paul Mohr, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1221 days.

(21) Appl. No.: 12/575,093

(22) Filed: Oct. 7, 2009

(65) Prior Publication Data

US 2011/0082369 A1    Apr. 7, 2011

(51) Int. Cl.
    A61B 5/05    (2006.01)
(52) U.S. Cl.
    USPC ........... 600/407; 600/420; 600/426; 600/447; 600/160
(58) Field of Classification Search
    USPC .......................... 600/407, 420, 426, 447, 160
    See application file for complete search history.

(56) References Cited

U.S. PATENT DOCUMENTS

| | | | |
|---|---|---|---|
| 4,786,813 A | 11/1988 | Svanberg et al. | |
| 4,951,133 A | 8/1990 | Onoda | |
| 5,133,605 A | 7/1992 | Nakamura | |
| 5,177,605 A | 1/1993 | Takahashi et al. | |
| 5,445,157 A | 8/1995 | Adachi et al. | |
| 5,711,755 A | 1/1998 | Bonnell et al. | |
| 5,944,653 A | 8/1999 | Bonnell et al. | |
| 6,161,031 A * | 12/2000 | Hochman et al. | 600/407 |
| 6,293,911 B1 | 9/2001 | Imaizumi et al. | |
| 6,652,452 B1 | 11/2003 | Seifert et al. | |
| 6,678,398 B2 | 1/2004 | Wolters et al. | |
| 7,480,402 B2 | 1/2009 | Bar-Zohar et al. | |
| 7,627,365 B2 * | 12/2009 | Chance | 600/475 |
| 7,668,587 B2 * | 2/2010 | Benaron et al. | 600/476 |
| 2005/0182321 A1 | 8/2005 | Frangioni | |
| 2010/0262017 A1 | 10/2010 | Frangioni | |

FOREIGN PATENT DOCUMENTS

| | | | |
|---|---|---|---|
| IL | WO2006111965 A2 | 10/2006 |
| US | WO2005034747 A1 | 4/2005 |

OTHER PUBLICATIONS

Allen, Thomas J. and Paul C. Beard, "Pulsed near-infrared laser diode excitation system for biomedical photoacoustic imaging," Optics Letters, vol. 31, No. 23, Dec. 1, 2006, pp. 3462-3464.

Vertut, Jean and Phillipe Coiffet, *Robot Technology: Teleoperation and Robotics Evolution and Development*, English translation Prentice-Hall, Inc., Inglewood Cliffs, NJ, USA 1986, vol. 3A, 332 pages.

Xu, Chenyang et al., "Near-infrared dyes as contrast-enhancing agents for spectroscopic optical coherence tomography," Optic Letters, vol. 29, No. 14, Jul. 15, 2004, pp. 1647-1649.

(Continued)

*Primary Examiner* — Joel Lamprecht

(57) ABSTRACT

In one embodiment of the invention, an apparatus includes a display device. The display device displays a desaturated image of tissue captured in the visible electro-magnetic (EM) spectrum from a body cavity; and a first color enhanced image combined with the desaturated image. The first color enhanced image represents the first data captured from the body cavity outside the visible electromagnetic spectrum. The relative brightness between the desaturated image and the first color enhanced image is set to emphasize the first data over the tissue captured in the visible electromagnetic spectrum to provide improved information content.

31 Claims, 10 Drawing Sheets
(7 of 10 Drawing Sheet(s) Filed in Color)

(56) References Cited

OTHER PUBLICATIONS

Kalitzeos, Angelos A. et al., "Enhancement of Cancerous/Normal Tissue Contrast via Combined White Light and Fluorescence Image Processing: Initial Investigation ex vivo," European Conference on Biomedical Optics (ECBO), Munich, Germany, Jun. 14, 2009, Tissue and Specimen Imaging (TSII), in Novel Optical Instrumentation for Biomedical Applications IV, C. Depeursinge and I. Vitkin, eds., vol. 7371 of Proceedings of SPIE-OSA Biomedical Optics (Optical Society of America, 2009), pp. 73710N-1 -73710N-4.

PCT/US10/50980 International Search Report and Written Opinion of the International Searching Authority, mailed Feb. 16, 2011, 11 pages.

* cited by examiner

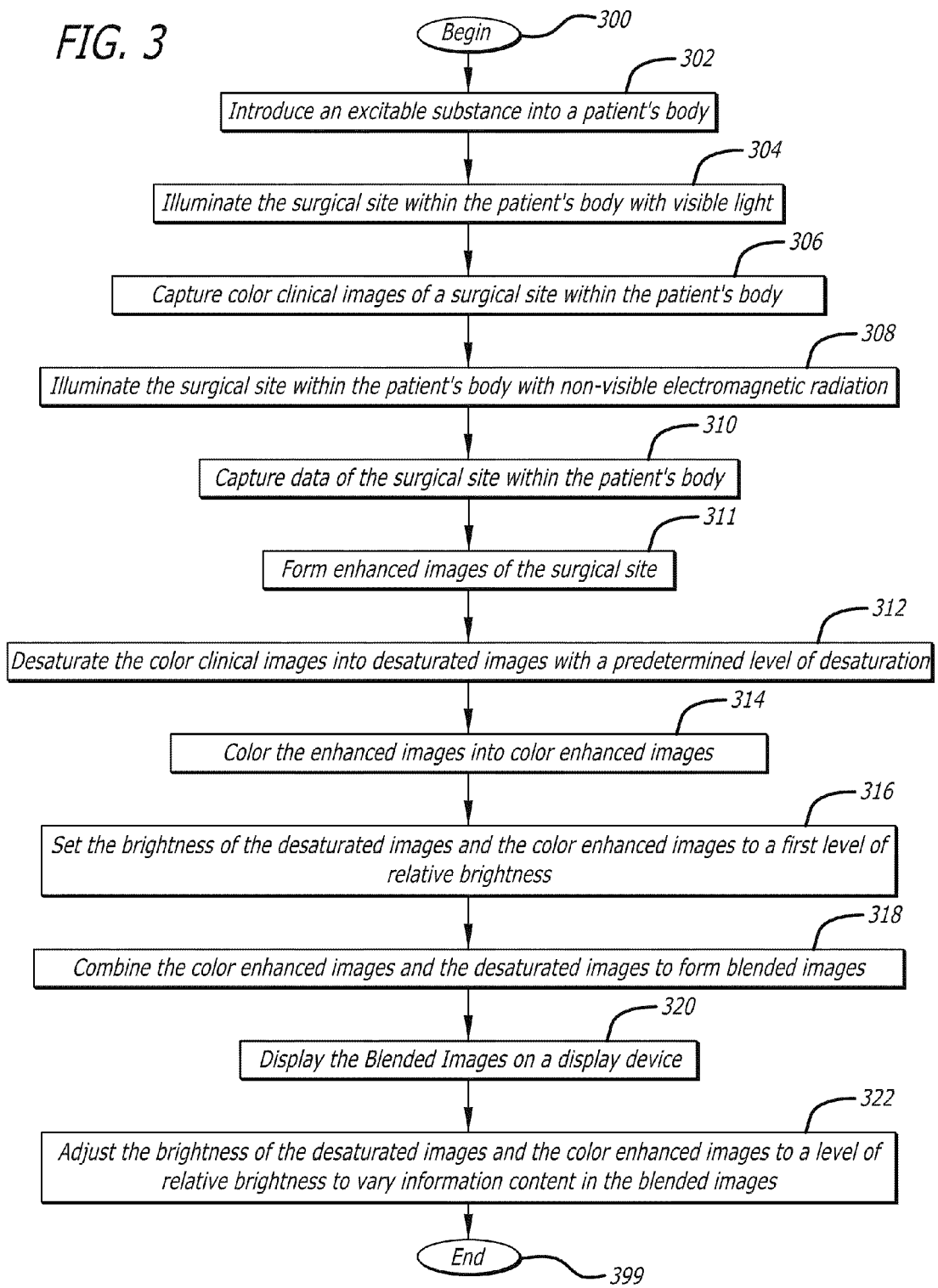

METHODS AND APPARATUS FOR DISPLAYING ENHANCED IMAGING DATA ON A CLINICAL IMAGE

FIELD

The embodiments of the invention generally relate to displaying medical images.

BACKGROUND

Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

To view a surgical site, an endoscopic camera with an illumination means may be inserted into a patient's body to capture color images of the surgical site. The color images of the surgical site may be shown to a surgeon on a monitor or a display.

Additional image information of the surgical site may be simultaneously displayed to the surgeon by use of a picture in picture (PIP) display. The additional image information may be useful to the surgeon to improve the surgical outcome. However, the smaller picture of a PIP display may be too small to show a desirable level of detailed information. Moreover with separate image frames, a surgeon mentally fuses the two separate images or imaging modalities together, which can be fatiguing. Alternatively, additional image information may be shown full screen by switching back and forth between the color images and the alternate additional image being displayed on the display device. However, switching back and forth between images takes time and can make surgery less efficient as a result. Moreover, a surgeon may fail to switch back to white light imaging and cut more than necessary or accidentally damage vital tissue while in an alternate imaging mode.

It is desirable to provide more efficient and safer minimally invasive surgery.

BRIEF SUMMARY

The embodiments of the invention are summarized by the claims that follow below.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 3 is a flow chart illustrating elements of imaging methods for embodiments of the invention.

Similar reference numbers in the different drawings are associated with the same or similar elements but may have a different configuration.

DETAILED DESCRIPTION

Figure 1:
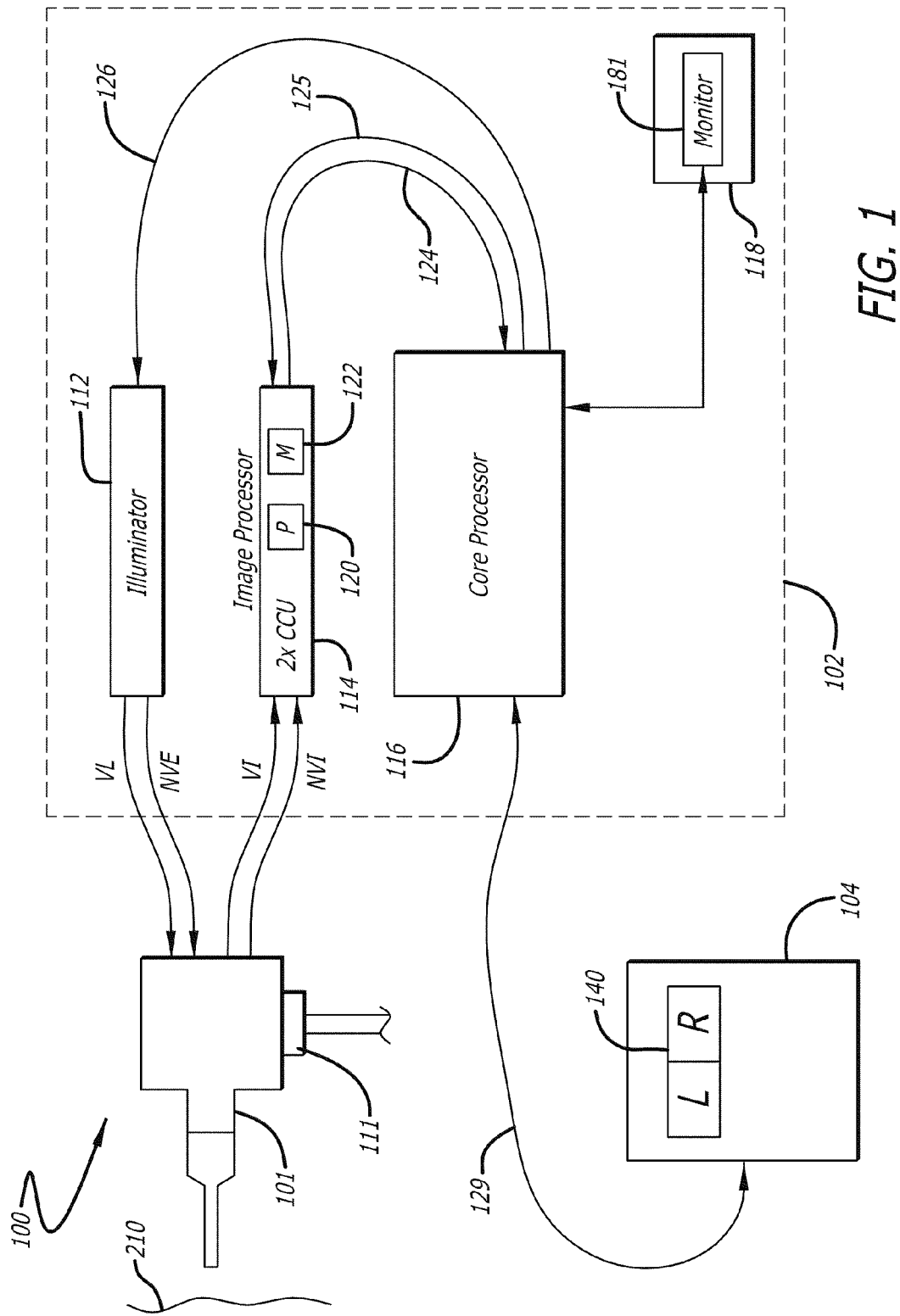
FIG. 1 is a block diagram of an imaging system for minimally invasive surgery.

This detailed description describes exemplary implementations that are illustrative of the invention, and so is explanatory and not limiting. The invention is limited only by patented claims. In the drawings, some elements have been omitted to more clearly show the embodiments of the invention.

Introduction

The embodiments of the invention are aimed at improving the clinical utility of the simultaneous display of a reflected white light image of tissue, and a separately or simultaneously acquired enhanced image of tissue in the same surgical site. The enhanced image of tissue may be captured with technologies such as, but not limited to, near-infrared (NIR) fluorescence, visible light fluorescence, multispectral imaging, fluorescence lifetime imaging, or a raster scan of non-visible light characteristics that contains clinical information with spatial variation. In addition, the enhanced image may be of an image constructed by overlaying point measurements of different types of measurable tissue parameters such as tissue impedance, point detection of cancer, or certain cell types on the clinical white light image.

Generally in one embodiment of the invention, a method of displaying is disclosed in which a visible, white light, or color clinical image is desaturated toward a grayscale or a black/white image that is displayed to the surgeon or clinician instead of a color reflected white light image. Desaturation pushes the red, green, and blue hues towards gray thereby removing color from an image. Enhanced information regarding the clinical image is captured using one or more enhanced imaging techniques and represented in the visible spectrum with one or more colors in registration with the desaturated white light image. When the enhanced information, typically invisible to the unaided eye, is represented in the visible spectrum it is false colored. Examples of false colors (also referred to as enhancement colors) to color the enhanced images are, but not limited to, green, blue, and purple that may be used to represent one or more types of signals in the non-visible electromagnetic spectrum detected by the enhanced imaging technology in the enhanced images. The color version of the enhanced image is registered to the desaturated white light clinical image and blended with, superimposed on, or overlaid on top of (alternatively referred to as being combined with) the desaturated clinical image.

The combination of these two images in a blended image is displayed to the surgeon to increase the amount of clinically relevant information, and to improve the detectability of low signal levels in the color enhanced images of the surgical site during surgery.

As the clinical image is desaturated, the color information in the image is removed but there is little loss in detail. The desaturated clinical image is sufficient to identify anatomy, tissue landmarks, and surgical instruments so that it allows safe manipulation thereof. Moreover with a desaturated clinical image, there is no loss in contrast of the enhanced image due to interference by a color representation of a white light clinical image. The color enhanced image overlaid onto the desaturated clinical image provides improved information content regarding the surgical site to reduce the risk of injury to the patient and improve surgical efficiency.

The color enhanced image can be overlaid onto the desaturated clinical image with a preset relative brightness to emphasize the enhanced information from the non-visible information about the tissue over the visible image of the tissue. Alternatively, a user interface device may be provided, such as a slide-type control, to allow blending of the two images so that a continuous variation of the relative brightness of the two images may be varied. The adjustment in relative brightness through this blending mode allows a user tailor the overlay brightness to match the clinical requirements of the task being performed with the enhanced imaging information. For example, when looking for thin, faint lines, the user can weight the relative brightness more strongly towards the enhanced image. When excising a brightly glowing large mass in the enhanced image, for example, the relative brightness image can be weighted more strongly towards the desaturated white light image.

Imaging System

Referring now to FIG. 1, a block diagram of an imaging system 100 for minimally invasive surgery is illustrated. The imaging system 100 includes an endoscopic camera 101, a vision control cart 102, and a surgeon console 104 coupled together as shown.

The endoscopic camera 101 includes a mechanical interface to detachably couple to a robotic arm 111 of a patient side manipulator so that it may be moved around within a surgical site of a patient. The endoscopic camera 101 is supported by the robotic arm 111 over a surgical site 210 within a body cavity of a patient to capture digital images therein.

The vision control cart 102 includes an illuminator 112, an image processor 114, a core processor 116, and a monitor 118. The endoscopic camera 101 is coupled to the illuminator 112 to receive visible light (VL) and direct it out of its tip into a surgical site to visibly illuminate tissue for capture with a color or spectral camera. The endoscopic camera 101 may also be coupled to the illuminator 112 to receive non-visible electromagnetic radiation (NVE) and direct it out of its tip into the surgical site to excite a material to fluoresce tissue for capture with a sensor or spectral camera. The endoscopic camera 101 captures one or more frames of a color visible image (VI) of tissue within the surgical site in response to the visible light (VL) and couples them into the image processor 114. The endoscopic camera 101 may further capture one or more frames of non-visible spatially encoded data from the tissue within the surgical site in response to the non-visible electromagnetic radiation (NVE) and couple the data into the image processor 114. For stereo imaging, the endoscopic camera 101 is a stereo camera for concurrently capturing left and right images of the surgical site. While the endoscopic camera 101 and its sensors may be used to capture optical non-visible images (e.g., near infrared, ultraviolet), other imaging devices and techniques may be used to capture other non-visible spectrum data, such as but not limited to, spectroscopic data, Raman scattering values, impedance data, two-photon fluorescence, ultrasound, gamma radiation and/or X-ray images whose data may be represented as an image in the visible spectrum and combined with the desaturated image. Additionally, light may be captured which covers all or a portion of the entire image and analyzed to create clinically relevant two dimensional (2D) images. These 2D images may capture features extracted from light properties such as polarization, scattering, and other similar characteristics related to the interaction of light and tissue where the tissue may be augmented by various clinically relevant markers. The enhanced image may be an image which has been computed for a series of visible images. For example, a series of images may be used to compute blood flow which can then be represented as a 2D image.

The illuminator 112 may generate the visible light (VL), a light generated in the visible electromagnetic radiation spectrum, and the non-visible electromagnetic radiation (NVE) in response to control signals 126 that may be received from the core processor 116. The illuminator 112 may generate the visible light (VL) and the non-visible electromagnetic radiation (NVE) concurrently to capture frames of the color visible images (VI) in synch with capturing the non-visible spectrum data and forming frames of enhanced images in response to the control signals. Alternatively, the illuminator 112 may alternate the generation of the visible light (VL) and the non-visible electromagnetic radiation (NVE) to capture frames of the color visible images (VI) out of synch with capturing the non-visible spectrum data and forming frames of enhanced images in response to the control signals.

The visible light (VL) and the non-visible electromagnetic radiation (NVE) may be coupled into the endoscopic camera 101 by one or more optical fibers or bundles of optical fibers. Similarly, the full color visible images (VI) of visible tissue captured within the surgical site and coupled into the image processor 114 via an optical fiber or captured by a sensor and coupled into the image processor by a wire cable. The non-visible spectrum data of the tissue within the surgical site may also be coupled into the image processor 114 via an optical fiber or captured by a sensor and coupled into the image processor by a wire cable. Electromagnetic radiation captured by one or more sensors may be binned out into the visible red, green, blue EM spectrum and the non-visible EM spectrum (e.g., near-infra-red).

The image processor 114 includes one or more processors P 120 to process the captured images and one or more storage devices (e.g., memory) M 122 to store one or more frames of image data. For stereo imaging, the image processor 114 may include a pair of processors P 120 to process left and right captured images and a pair of storage devices (e.g., memory) M 122 to store left and right image frames.

In the enhanced display mode, the one or more processors P 120 of the image processor 114 may perform the pixel manipulation of each frame of digital image data in order to perform the image processing and display methods disclosed herein. The image processor 114 receives commands 125 from the core processor 116 and couples the images 124 to the core processor 116 for display on a display 140 of the surgeon console 104 and/or the monitor 118 of the control cart 102. Alternatively, the core processor 116 may receive the digital images and perform the pixel manipulation of each frame of digital image data in order to perform the image processing and display methods disclosed herein.

The surgeon console 104 may be coupled to the core processor 116 over a fiber optic cable 129 for high-speed communication of digital control and image information. The surgeon console 104 may include a stereo display device 140 to display left and right stereo images to the surgeon. The stereo display device 140 may display left and right blended images in accordance with the display method disclosed herein.

Further information regarding minimally invasive surgical systems may be found for example in U.S. patent application Ser. No. 11/762,165, entitled MINIMALLY INVASIVE SURGICAL SYSTEM, filed by David Q. Larkin et al. on Jun. 13, 2007; and U.S. Pat. No. 6,331,181, entitled SURGICAL ROBOTIC TOOLS, DATA ARCHITECTURE, AND USE, issued to Tierney et al. on Dec. 18, 2001, both of which are incorporated herein by reference.

Illuminating Non-Visible Characteristic Tissue Features

Figure 2:
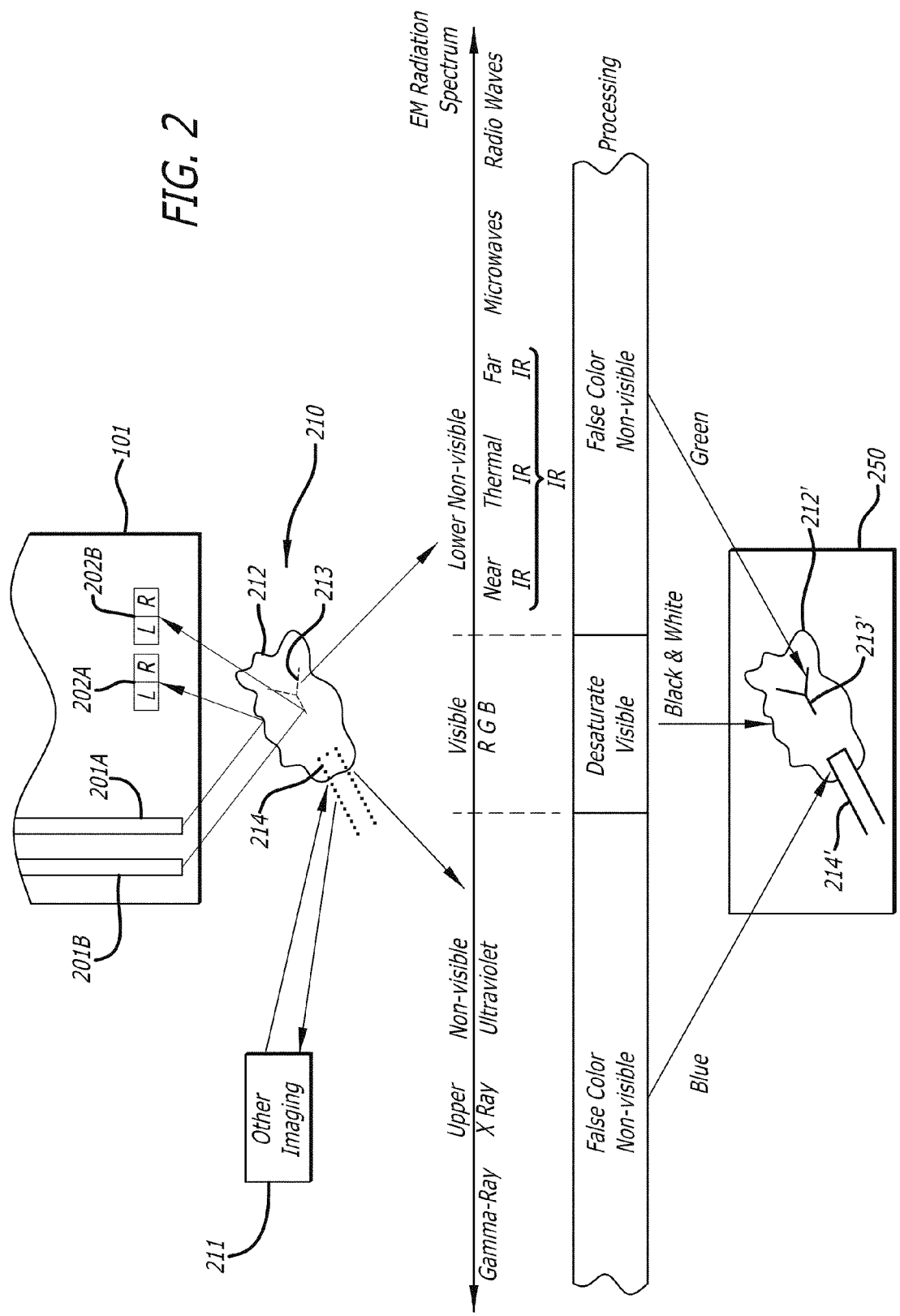
FIG. 2 is a pictorial diagram of aspects of embodiments of the invention.

Referring now to FIG. 2, a pictorial diagram of aspects of embodiments of the invention is illustrated. The endoscope 101 may include one or more optical fibers 201A-201B to direct and emit visible light (VL) and non-visible electromagnetic radiation (NVE) into a surgical site 210. The endoscope 101 may include a sensor 202A to capture electromagnetic radiation in the visible spectrum, such as a camera. The sensor 202A may be a stereo color camera to capture visible stereo color images. The endoscope 101 may further include another sensor 202B to capture electromagnetic radiation in the non-visible spectrum or other types of information (e.g. ultrasound) normally invisible to the naked eye. For example, the sensor 202B may be a near-infrared (NIR) detector to capture NIR enhanced images of the surgical site. Alternatively, the endoscope 101 may be a conduit to direct the visible light and the non-visible spectrum data back to external sensors/camera outside the body of the patient.

The surgical site 210 includes tissue 212 that can reflect a white light or color image when illuminated by visible light. The surgical site 210 also has characteristic tissue features 213, 214 that are not visible to the unaided eye when illuminated by light in the visible electromagnetic spectrum.

The various non-visible characteristic tissue features 213, 214 may be illuminated by non-visible electromagnetic radiation (NVE) with or without a fluorescing, emitting, tracing, or reflecting material (collectively referred to as a biomarker). In some cases, the non-visible characteristic tissue features may be biochemically tagged with a fluorescing, emitting, tracing or reflecting material or compound (collectively referred to as a biomarker) which may be excited by visible light or electromagnetic radiation (VL) or non-visible electromagnetic radiation (NVE), so that it may be captured by a visible light camera or sensor. In other cases, some non-visible characteristic tissue features may be biochemically tagged with a fluorescing, emitting, tracing, marking, or reflecting material/compound (collectively referred to as a biomarker), excited by non-visible electromagnetic radiation (NVE) so that it emits at wavelength of the non-visible electromagnetic radiation (NVE) and captured by a sensor sensitive to that wavelength.

Tissue that is not visible with reflected white light may be made imageable in various ways. For example, tissue that is not visible with reflected white light may be made imageable by injecting fluids or tagging tissue of a patient with a fluorescing, emitting, tracing material, dye or compound (collectively referred to as a biomarker) and illuminating it with or exposing it to electromagnetic radiation. A fluorphore in a biomarker tags a molecule so that it absorbs EM radiation about an excitation wavelength and re-emits EM radiation about an emission wavelength. One example of a fluorescing material or compound (a biomarker) is indocyanine green (ICG) that fluoresces to emit photons or electromagnetic radiation in a non-visible wavelength when excited by near-infrared (NIR) electromagnetic radiation. There are various fluorescent compounds that may be used to tag tissues of interest that excite at desirable excitation wavelengths and emit at desirable emission wavelengths. Exemplary fluorophores, emitters, tracers, markers, etc. (collectively referred to as a biomarker) that may be used are listed in the Appendix which is attached hereto and incorporated herein by reference.

Tissue that is not visible with reflected white light may also me made imageable by injecting a material, dye, or compound (collectively referred to as a biomarker) which binds to specific tissue types and spontaneously emits EM radiation, such as a radiopharmaceutical or radiotracer used in positron emission tomography (PET).

Other imaging sources 211 (e.g., X-rays, ultrasound) outside the visible EM spectrum may be used to illuminate some non-visible characteristic tissue features 214 (e.g., bone tissue) and capture enhanced images, with or without a biomarker, for combining with the clinical images of visible tissue. For example, bone tissue may be captured with X-rays within a surgical site during surgery without a biomarker. As another example, sub-surface tissue within a surgical site may be captured during surgery with ultrasound without an added fluorescing, emitting, tracing, marking or reflecting material/compound (collectively referred to as a biomarker), The visible tissue 212 is illuminated by visible light, electromagnetic radiation in the visible portion of the electromagnetic radiation spectrum (VL) that human eyes can perceive. The illumination may be made of white light which may be broad spectrum or may be a mixing of several discrete narrow spectrum colors, including one or more of the primary colors of red (R), green (G), and blue (B). The visible portion of the electromagnetic radiation spectrum ranges from approximately 400 nano-meters (nm) to 700 nm in wavelength. Characteristic tissue features tagged with a fluorescing, emitting, tracing, marking or reflecting material or compound (collectively referred to as a biomarker) excitable by visible light, may be captured by a camera or a visible light sensor if it fluoresces or emits in the visible electromagnetic radiation spectrum.

Characteristic tissue features 213, 214, not visible with reflected white light, may also be tagged and illuminated by electromagnetic radiation outside the visible EM spectrum in the lower or upper non-visible portions of the electromagnetic radiation spectrum (NVE) that unaided human eyes can't perceive. The lower and upper non-visible portions of the electromagnetic radiation spectrum reside outside the visible portion of the electromagnetic radiation spectrum. The upper non-visible portion of the electromagnetic radiation spectrum ranges from approximately 400 nano-meters (nm) to one tenth of an angstrom (A) in wavelength including gamma-rays, x-rays, and ultraviolet electromagnetic radiation. The lower non-visible portion of the electromagnetic radiation spectrum ranges from approximately 600 nano-meters (nm) to ten meters (m) in wavelength including infrared (near infrared, thermal infrared, far infrared), microwaves, and radio waves. Near infrared EM radiation, with a wavelength range approximately between 600 nm to 1200 nm, may be preferable in some cases as many biological tissues are more transparent at these wavelengths than in the visible spectrum so that tissue features or structures below the surface that are tagged with a biomarker may be more readily imaged.

With a fluorescing or reflecting material or compound excited by non-visible electromagnetic radiation, tissue not visible in a reflected white light image may fluoresce and emit EM radiation in the non-visible electromagnetic spectrum. A sensor sensitive to non-visible electromagnetic radiation may capture the EM radiation in the non-visible electromagnetic spectrum allowing construction of an enhanced image for display in the visible spectrum. Alternatively, if the fluorescing or reflecting material or compound excited by non-visible electromagnetic radiation can emit some EM radiation in the visible electromagnetic spectrum, it may be captured by a camera or sensor sensitive in the visible light spectrum. Regardless, non-visible information from the surgical site in the non-visible spectrum is captured and represented in the visible spectrum within a digital image.

The embodiments of the invention generally desaturate images of tissue captured in the visible portion of the electromagnetic spectrum, move images of tissue captured in the non-visible portion of the electromagnetic spectrum into the visible portion of the electromagnetic spectrum through colorization, and combine or overlay the colorized images onto the desaturated images to form a blended image for display on a display device.

For example, the image of visible tissue 212 illuminated by light in the visible electromagnetic spectrum and captured by a color camera is desaturated (has its color reduced) towards a grey scale, black/white, or monochrome image 212'. The red, green, blue color data in each pixel of the visible tissue image 212 may be equally reduced towards grey scale or black/white.

The non-visible characteristic tissue feature 213 that is not visible in the visible spectrum image may be illuminated by non-visible electromagnetic illumination and captured with a sensor. The captured data can be enhanced by forming an enhanced image and then coloring it with a first visible color to form a first colored enhanced image. For example, the characteristic tissue feature 213 not visible in the visible spectrum may be moved into the visible electromagnetic spectrum by coloring it with the color green to form a green colored enhanced image 213'. Non-visible characteristic tissue feature 214 not visible in the visible spectrum may be illuminated by non-visible electromagnetic illumination and captured with a sensor. The captured data can then be enhanced by forming an enhanced image and then coloring it with a second visible color, such as a second visible color, to form a second colored enhanced image. For example, the non-visible characteristic tissue feature 214 may be moved into the visible electromagnetic spectrum by coloring it with the color blue to form a blue colored enhanced image 214'. The green colored enhanced image 213' and the blue colored enhanced image 214' may be overlaid onto the grey scale or black and white image 212' to form a blended image 250 of the surgical site 210.

The visible tissue 212 may be surface tissue while the various non-visible tissue 213, 214 may be sub-surface tissue that is found below the surface tissue. As a result, the image of the sub-surface tissue may be faint and spread out when captured. Adjustment in the relative brightness or desaturation levels may be used to compensate for a faint image.

Display Methods

Referring now to FIG. 3, a flow chart illustrates elements of imaging methods in an enhanced display mode. With different types of enhanced images being captured, one or more of the elements shown in FIG. 3 are optional in performing imaging methods. The process begins at process block 300 and goes to process block 302.

At process block 302, an excitable substance may be introduced into a patient's body that can be excited by electromagnetic (EM) radiation in either the upper or lower non-visible electromagnetic spectrum. Alternately, the introduced substance may spontaneously emit EM radiation, such as gamma rays, without external excitation. The process may then go to process block 304.

At process block 304, the surgical site within the patient's body is illuminated with visible light or electromagnetic radiation in the visible electromagnetic spectrum, such as a white light. The process then goes to process block 306.

Figure 4A:
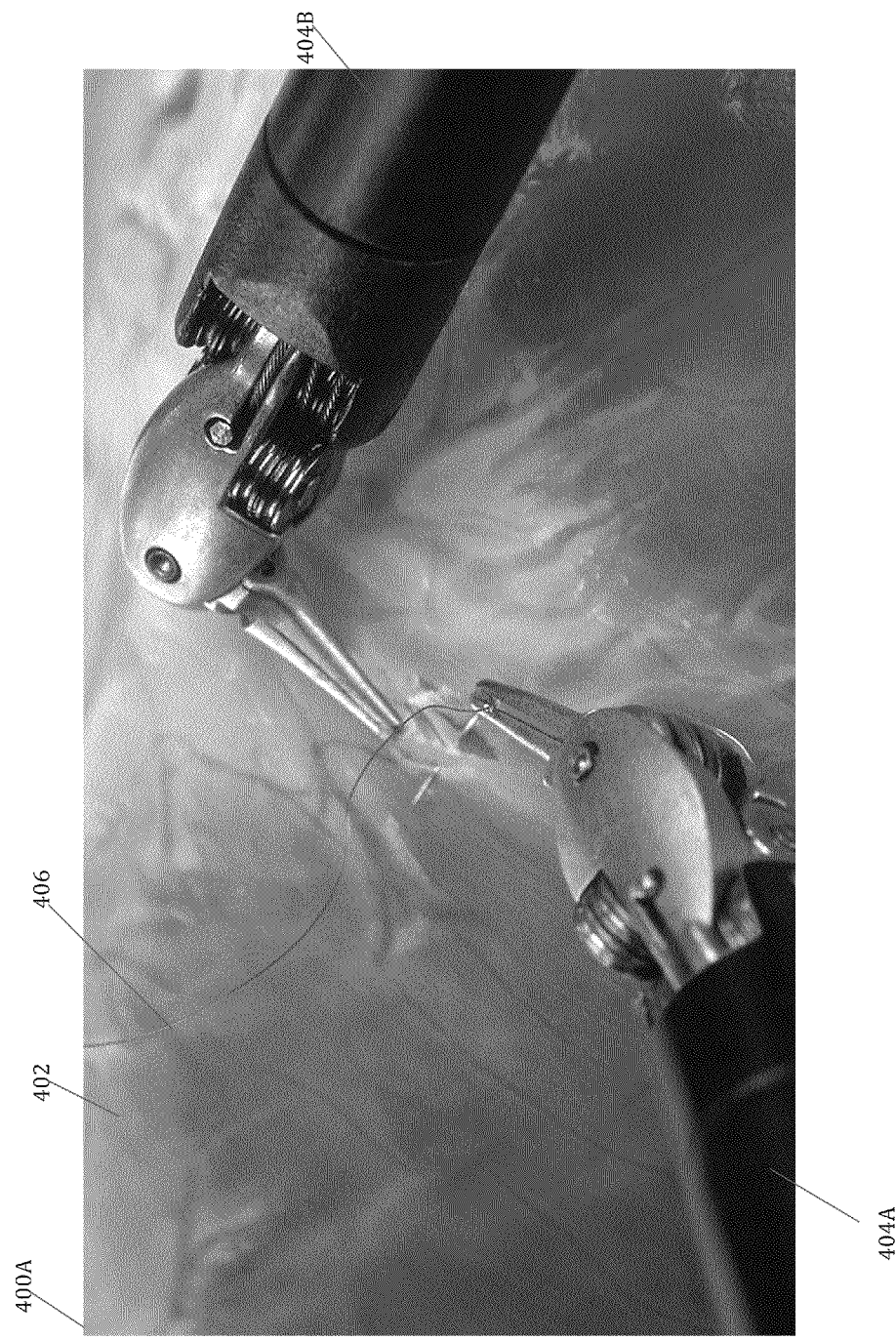
FIG. 4A is a color diagram illustrating capturing a visible white light color image of a surgical site.

At process block 306, color clinical images of the surgical site are captured within the patient's body with a sensor, such as a color CMOS (complementary metal oxide semiconductor) camera, in response to the visible electromagnetic radiation. FIG. 4A illustrates a color clinical image 400A captured by a color CMOS camera. The color clinical image 400 includes in color visible tissue 402, a pair of visible robotic surgical tools 404A-404B, and a visible needle and suture 406 that reflect light in the visible electromagnetic spectrum. The process then goes to process block 308.

At process block 308, the surgical site within the patient's body may be illuminated with or exposed to non-visible electromagnetic radiation in the upper and lower non-visible electromagnetic spectrum. The patient's body may be alternatively or concurrently be illuminated with or exposed to both visible and non-visible electromagnetic radiation over the electromagnetic spectrum. The process may then go to process block 310.

At process block 310, data to form enhanced images of the surgical site with the patient's body may be captured with a sensor in response to the non-visible electromagnetic radiation. The captured data may be referred to as non-visible spectrum data. Visible images and non-visible spectrum data of the surgical site may alternatively or concurrently be captured. For example, frames of visible images and data for the formation of enhanced images may be alternatively captured in the surgical site. The process then goes to process block 311.

Figure 5A:
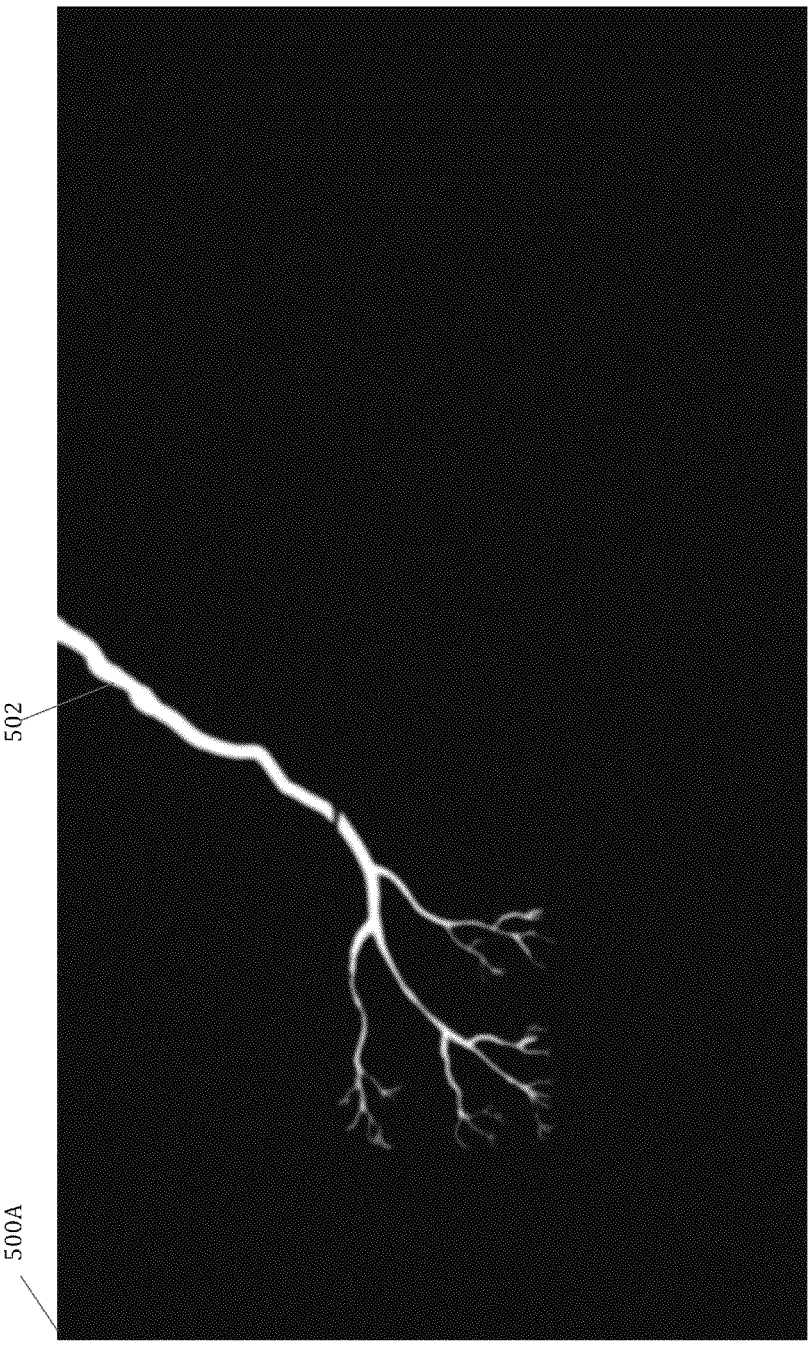
FIG. 5A is a black and white diagram illustrating capturing data in the non-visible spectrum and forming an image of a characteristic tissue feature within the surgical site.

At process block 311, the enhanced images are formed of the surgical site in response to the non-visible spectrum data. FIG. 5A illustrates an enhanced image 500A of the surgical site generated from the capture of data within a patient's body. The enhanced image 500A has yet to be colored. The enhanced image 500A includes a characteristic tissue feature 502, such as a blood vessel beneath the tissue surface, or other marked, excited, or spontaneously emitting tissue. The process may then go to process block 312.

Figure 4B:
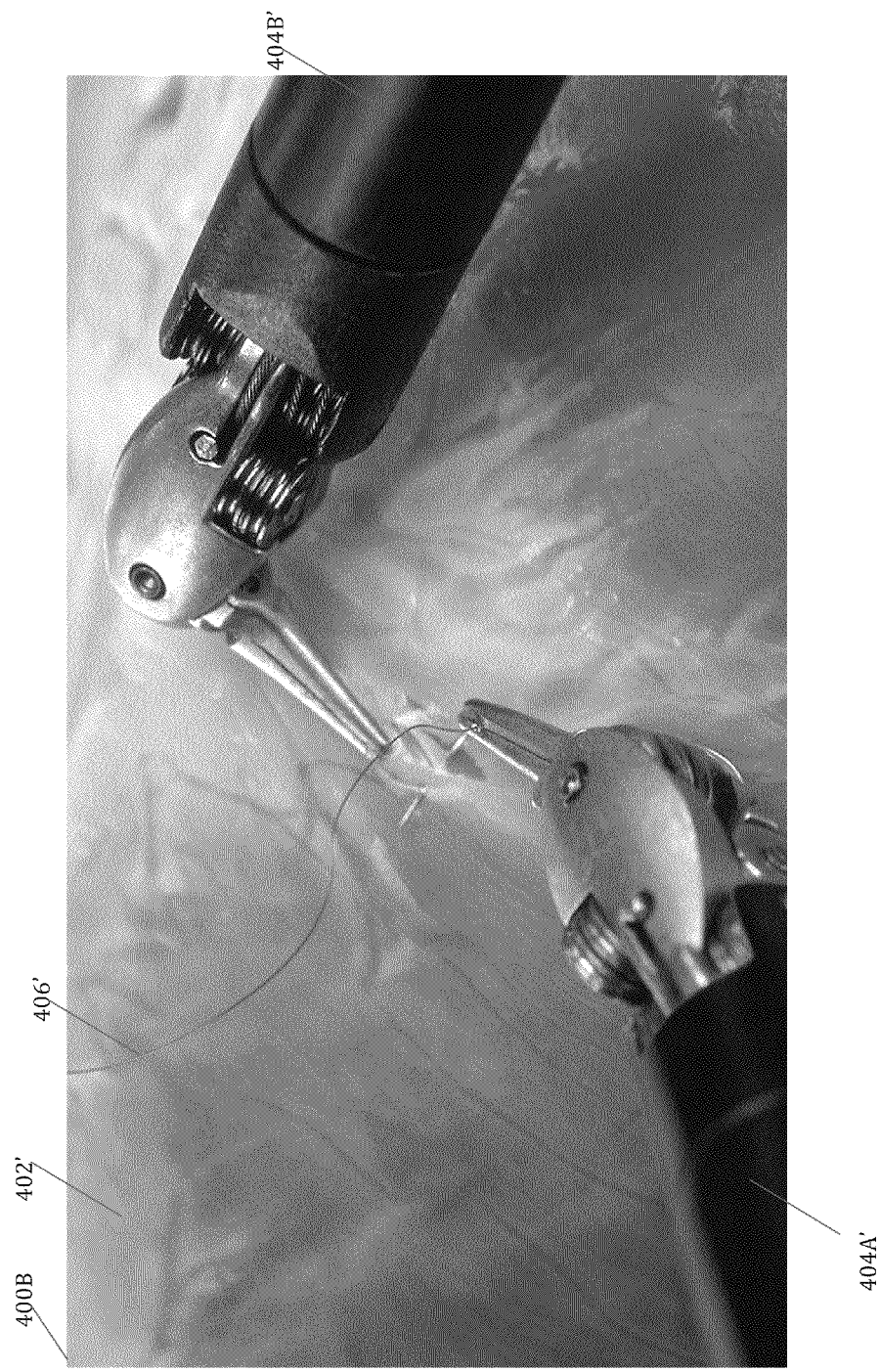
FIG. 4B is a non-color diagram illustrating the desaturating of the visible white light color image of FIG. 4A into a black and white or grey scale desaturated image.

At process block 312, the color clinical images 400A are desaturated (reduced in color towards black and white) into desaturated images with a predetermined level of desaturation. The level of desaturation (reduction in color) may be varied. FIG. 4B illustrates a desaturated clinical image 400B with reduced color from that of the color clinical image 400A of FIG. 4A. The visible tissue 402', the visible tools 404A'-404B', and the visible needle and suture 406' are reduced in color toward black and white or grayscale. The process then goes to process block 314.

Figure 5B:
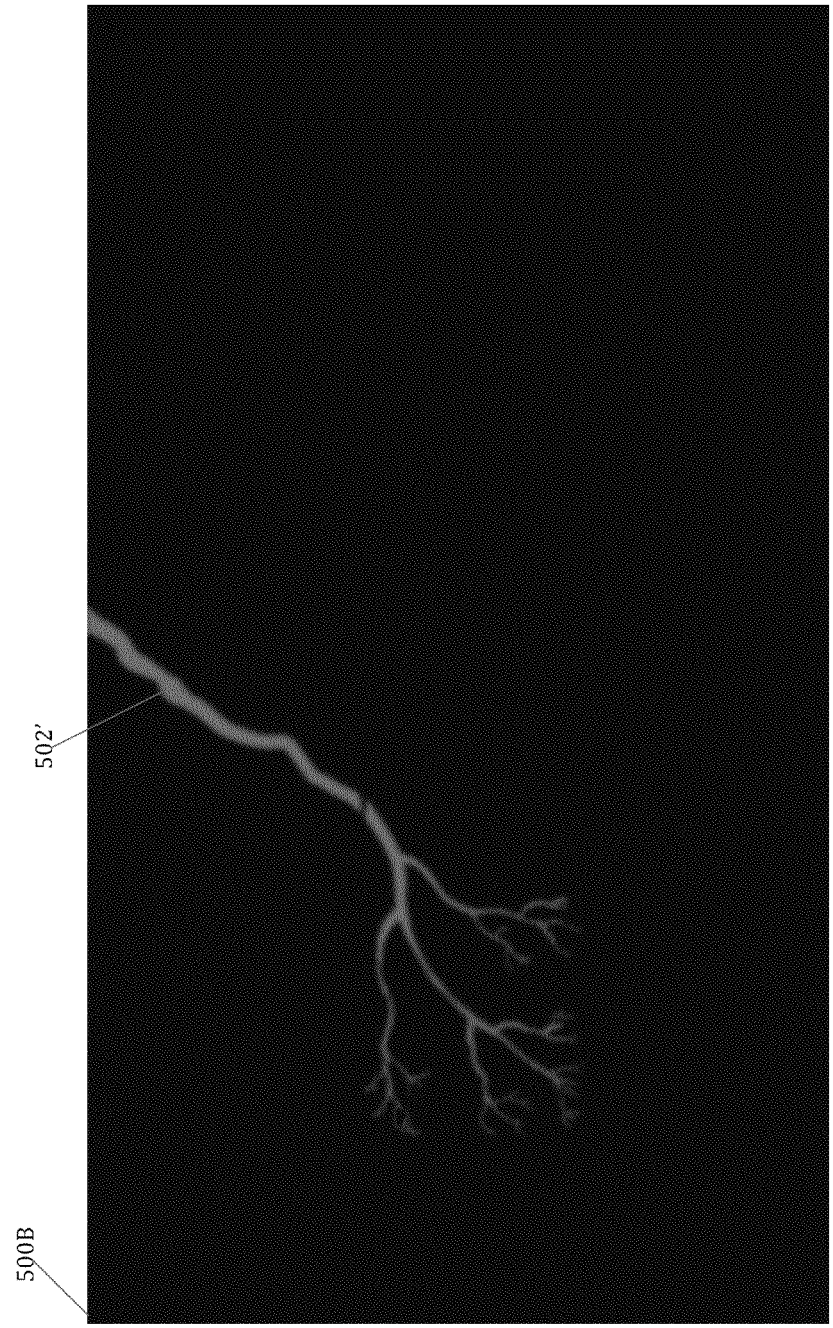
FIG. 5B is a diagram illustrating the coloring of the characteristic tissue feature of FIG. 5A to form a color enhanced image.

At process block 314, the enhanced images previously formed are colorized with a color to form color enhanced images. FIG. 5B illustrates a color enhanced image 500B. The characteristic tissue features 502 in the color enhanced image 500B are colorized with the color green. The process then goes to process block 316.

At process block 316, the brightness of the desaturated images 400B and the color enhanced images 500B is set to a first level of relative brightness. The brightness of the desaturated images and the brightness of the color enhanced images may be set independently to provide a first level of relative brightness. The process then goes to process block 318.

At process block 318, the color enhanced images are combined with (e.g., overlaid onto) the desaturated images to form blended images. The blended images have added information content over that of the color clinical images alone. The color emphasizes the information of the color enhanced images within the blended images.

Figure 6:
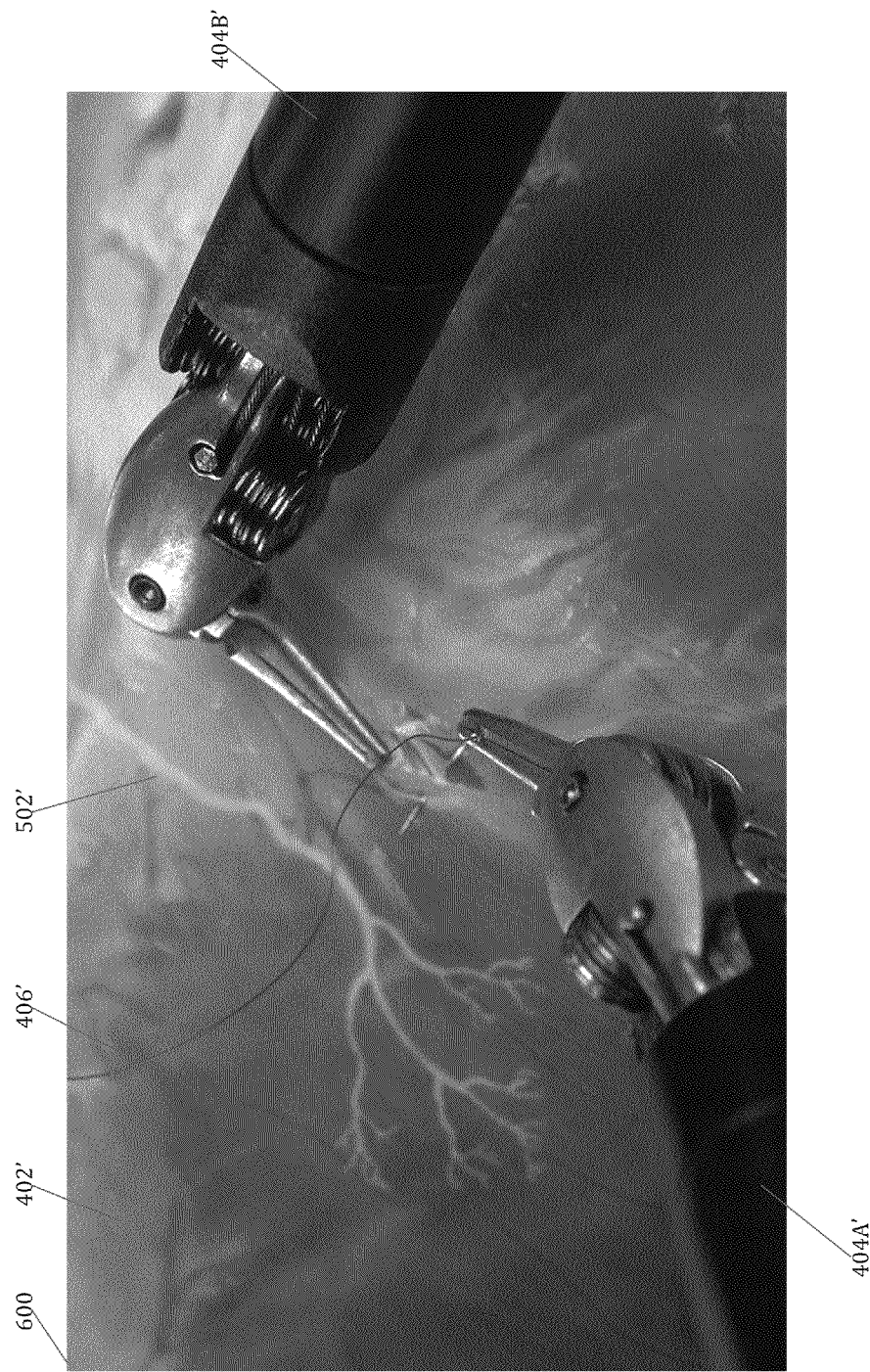
FIG. 6 is a diagram of a display of a blended image with the color enhanced image of FIG. 5B combined with (e.g., overlaid onto) the clinical image.

FIG. 6 illustrates a blended image 600. The blended image 600 includes the colored characteristic tissue features 502' of the color enhanced image 500B combined with the desaturated tissue features 402', tools 404A'-404B', and needle and suture 406' of the desaturated image 400B.

The color enhanced image 500B may be registered to the desaturated image 400B so that they can be combined together into the blended image 600. Spatial registration may be performed to combine the color enhanced image 500B and the desaturated image 400B together. Coordinate transformations may be computed between the different data sources if the images have different frame sizes or orientation to provide spatial registration. Temporal registration may also be performed to combine the color enhanced image 500B and the desaturated image 400B together if they are out of sync. Frames of images that are out of sync with respect to time may by synched up together to properly combine together frames of the color enhanced image 500B and the desaturated image 400B with respect to time. After combining the image information together, the process may then go to process block 320.

At process block 320, the blended images 600 are displayed on a display device such as the stereo viewer 140 of the surgeon console 104 and/or a different monitor or display device (e.g., monitor 181). The process may then go to process block 322.

At process block 322, the brightness of the desaturated images 400B and the color enhanced images 500B may each be adjusted in the blended images 600 to a level of relative brightness to vary information content in the blended images displayed on the display device. A software and/or physical user interface may be used to adjust the brightness of each of the desaturated images 400B and the color enhanced images 500B or the relative brightness between them.

One or more of the processes may be repeated over and over for each frame to continuously display blended images 600 on the display device until the surgery ends or the color enhanced images 500B are no longer needed. In which case, the display mode of the imaging system may be switched back to a normal mode to display the color clinical images 400A of the surgical site without the enhanced images. The enhanced display mode process may then go to process block 399.

At process block 399, the process may end if the surgery is concluded or the processes are not repeated any further.

An alternate display method may be more specifically described with respect to a fluorescing image. The alternate display method may include obtaining a visible color image of a surgical site illuminated by visible light; desaturating the visible color image of the surgical site into a visible gray image; obtaining a fluorescent image of fluorescing tissue in the surgical site, wherein the fluorescing tissue appears in a visible color; and generating a displayable image comprising a combination of the visible fluorescent image and the visible gray image.

User Interface

As mentioned previously, a software and/or physical user interface may be used to support an enhanced display mode for combining and displaying together the desaturated images and the color enhanced images.

The enhanced display mode may selectively be entered at the surgeon console by a predetermined sequence selection of user interface switches generating a control signal, such as by selection of switches in the left and right master grips and/or foot pedals of the surgeon console 104. Alternatively, a menu item in a menu list may be selected by a master grip in a masters-as-mice mode may be used to generate a control signal to selectively enter the enhanced display mode. For example, a master grip switch described in application Ser. No. 12/400,738, entitled USER INTERFACES FOR ELECTROSURGICAL TOOLS IN ROBOTIC SURGICAL SYSTEMS, filed by Paul Mohr et al. on Mar. 9, 2009, incorporated herein by reference, may be used to activate the enhanced display mode of the imaging system. The enhanced display mode may be selectively exited by entering the predetermined sequence selection of user interface switches for a second time to generate the control signal to return to normal display mode of color images of the surgical site.

In the enhanced display mode, a user interface may be provided to selectively control features thereof. Some of the controllable features in the enhanced display mode include the relative brightness between the colored enhanced images and the desaturated images, and/or the level of desaturation of the desaturated images.

Figure 7:
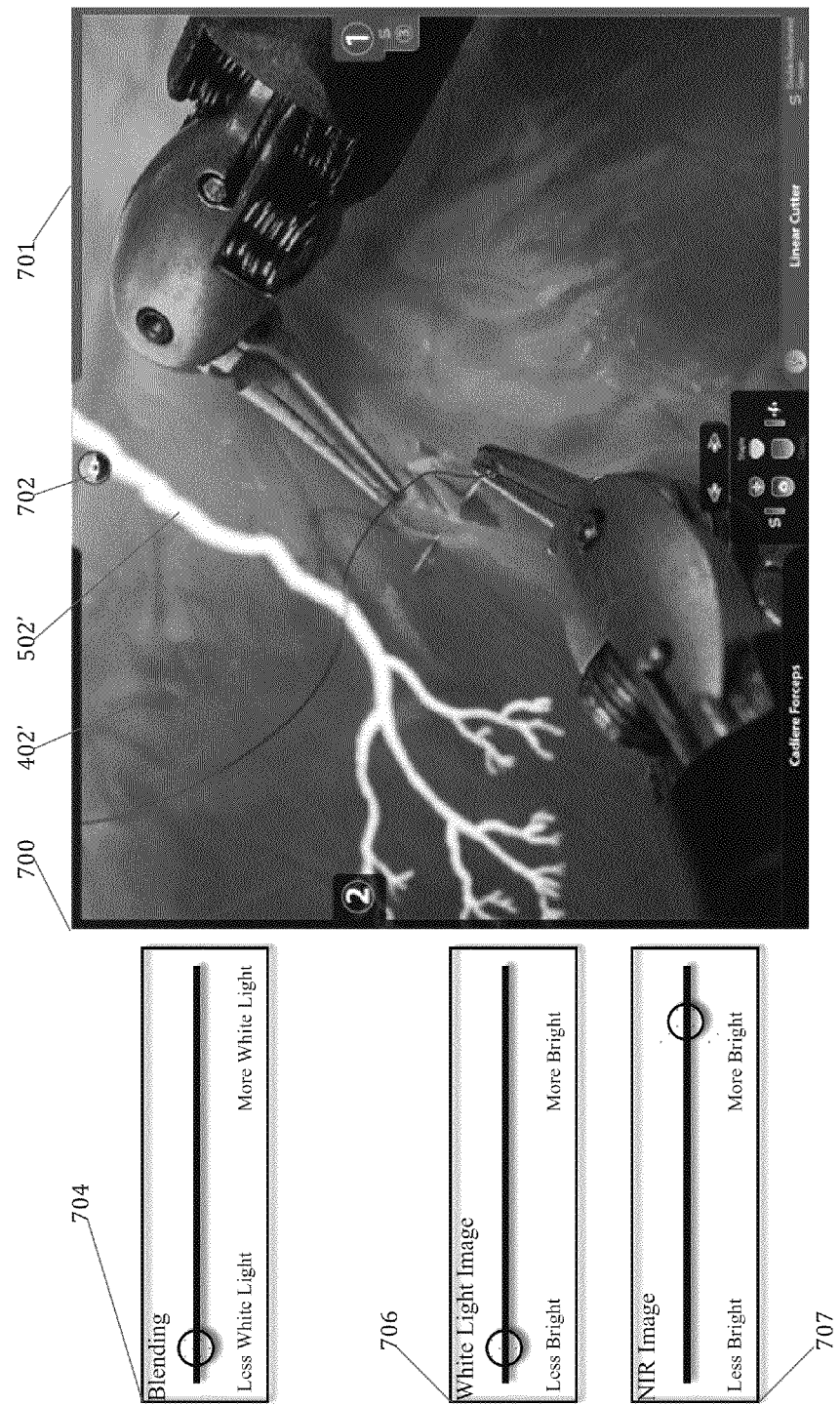
FIG. 7 is a diagram illustrating a user interface to adjust the brightness of the component images or the relative brightness between the component images in the blended image.

Referring now to FIG. 7, a display 700 is shown including a user interface 701 for an enhanced display mode. The user interface 701 may include an enhanced display icon 702 to indicate to the user what display mode (normal or enhanced) the imaging system is in. The user interface may further include a blending slider switch 704 to adjust the relative brightness between the desaturated image and the colored enhanced image. In FIG. 7, the slider switch 704 is adjusted to show less white light such that the colored enhanced image is emphasized over the desaturated image in the display 700. Alternatively, a pair of slider switches 706-707 may be provided in the user interface to separately adjust the brightness of the colored enhanced image and the brightness of the desaturated image to achieve a desired relative brightness between each. The brightness adjustment device may generate control signals to control the processing of the desaturated image as to how much white light is formed in the black/white or gray scale image. Alternatively, the brightness adjustment device may generate control signals to control the illuminator 112 to adjust the brightness level of the white light generated to illuminate the surgical site during image capture.

Figure 8:
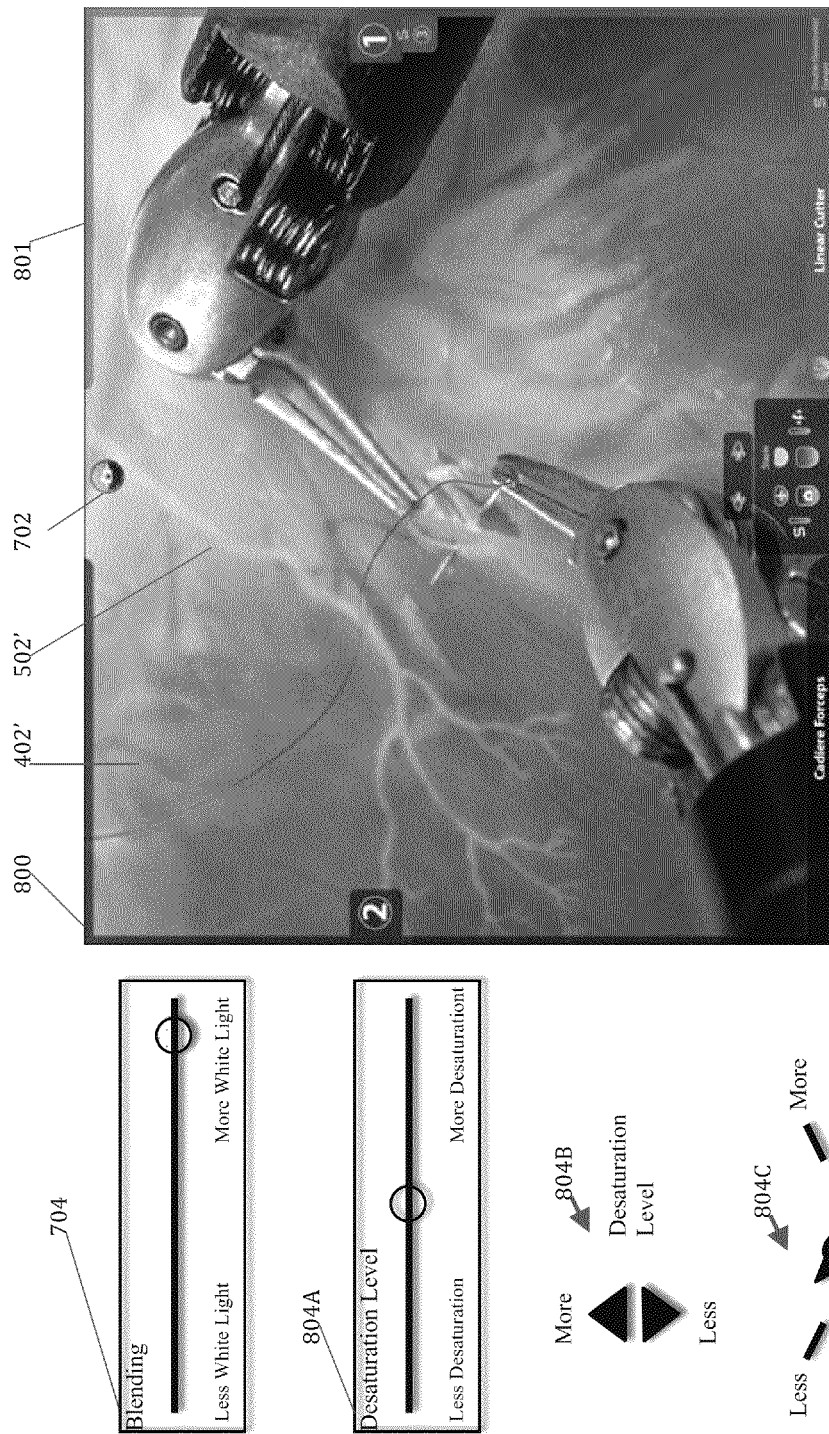
FIG. 8 is diagram illustrating a user interface that may be used to adjust the desaturation level of the color images of the surgical site into desaturated images.

Referring now to FIG. 8, a display 800 is shown including a user interface 801, similar to the user interface 701, including an icon 702 and a relative brightness selector 704. The user interface 801 further includes a user interface adjustment for desaturation of color images in addition to the adjustment for relative brightness (e.g., slider 704) described in reference to FIG. 7.

The user interface 801 may include a slider switch 804A to adjust the desaturation level of the desaturated images 402'. The desaturation adjustment device may generate control signals to control the processing of a visible color image into the desaturated image as to how much color is removed from the visible color image by reducing the red, green, blue (RGB) information in each pixel to form the desaturated image. The slider switch 804A is set so that the display 800 in FIG. 8 shows the desaturated images 402' with some color, but less than full color. Instead of a slider switch 804A, up and down push button switches 804B may be used to adjust the level of desaturation in the desaturated images 402'. Alternatively, a rotatable knob 804C may be used to adjust the level of desaturation in the desaturated images 402'.

In any case, a display device is disclosed that can display a desaturated image of tissue captured in the visible electromagnetic (EM) spectrum from a body cavity, and a first color enhanced image combined with the desaturated image. The first color enhanced image represents data captured from the body cavity outside the visible electromagnetic spectrum. A relative brightness between the desaturated image and the first color enhanced image can be set to emphasize the captured data over the tissue captured in the visible electromagnetic (EM) spectrum to provide improved information content to a user.

Conclusion

The disclosed methods provide sufficient clinical detail of the white light image to allow a user to avoid inadvertent collision of surgical instruments with tissue and gives sufficient landmarks to prevent the surgeon from getting lost in the anatomy while providing details of the information available in the enhanced image in a manner which makes it easy to distinguish the enhanced imaging information from details in the white light image.

One or more elements of the embodiments of the invention may be implemented in software so that one or more tasks may be automatically performed with a machine, such as a processor. When implemented in software, the elements of the embodiments of the invention are essentially the program instructions or code segments to perform the one or more tasks of the methods disclosed herein. For example, a machine readable media may have stored thereon instructions that when executed by a machine causes the machine to automatically perform operations including reducing color in color images captured of tissue in a surgical site in the visible electro-magnetic (EM) spectrum within a patient to form desaturated images; making non-visible characteristic tissue features captured in the surgical site visible in color enhanced images; and combining the color enhanced images and the desaturated images together to form combined images for display on at least one display device.

The program instructions or code segments can be stored in a processor readable medium for execution by the processor, such as processor 120 or core processor 116 shown in FIG. 1. The processor readable medium may include any medium that can store information, such as memory 122 for example illustrated in FIG. 1. Examples of a processor readable medium include an electronic circuit, a semiconductor memory device, a ROM, a flash memory, an erasable ROM (EROM), a floppy diskette, a CD-ROM, an optical disk, a hard disk, etc. The program instructions or code segments may be downloaded via computer networks such as the Internet, Intranet, etc.

While this specification includes many specifics, these should not be construed as limitations on the scope of the disclosure or of what may be claimed, but rather as descriptions of features specific to particular implementations of the disclosure. Certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. The claimed invention is limited only by patented claims that follow below.

APPENDIX

EXEMPLARY FLUOROPHORES, EMITTERS, TRACERS, ETC.

| Agent Name | Full name | Pathology Target | Type of marker (mechanism) |
|---|---|---|---|
| EF5 | 2-(2-nitro-1-H-imidazol-1-yl)-N-(2,2,3,3,3-pentafluoropropyl) acetamide | cancers, various | Binding |
| Superhance | | vasculature | Binding |
| A15 | A15 (NIRF agent) | thrombosis | Binding |
| AnxA5-QD-Gd | Annexin A5-quantum dot-DTPA-gadoliniumAnxA5-QD-Gd | Apoptosis | Binding |
| CREKA-SPIO-Cy7 | Cys-Arg-Glu-Lys-Ala-superparamagnetic iron oxide-Cy7 nanoparticlesCREKA-SPIO-Cy7 | Breast cancer | Binding |
| pLux-expressing E. coli | Luciferase-expressing Escherichia coliPLux-expressing E. coli | cancers, various | Binding |
| AnxCLIO-Cy5.5 | Annexin V-cross-linked iron oxide-Cy5.5AnxCLIO-Cy5.5 | apoptosis | Binding |
| Cy5.5-Annexin V | Cy5.5-Annexin V | Lung cancer | Binding |
| CLIO-EPPT | Cross-linked iron oxide-C-AHA-AREPPTRTFAYWGK(FITC) CLIO-EPPT | Pancreatic cancer | Binding |
| AOI987 | AOI987 | Alzheimer's disease | Binding |
| OsteoSense | | skeletal changes | Binding |
| Qsmart | | apoptosis | Binding |
| IntegriSense | | angiogenesis (tumor) | Binding |
| Cy7-DPA-Zn | Cy7-Bis-dipicolylamine-zincCy7-DPA-Zn | infection | Binding |
| SIDAG | 1,1'-bis-(4-sulfobutyl)indotricarbocyanine-5,5'-dicarboxylic acid diglucamide monosodium saltSIDAG | cancers, various | Binding |
| Vectibix | Panitumumab | Colorectal Cancer | Binding (antibody) |
| MDX1201 A488 | anti PSMA antibodyconjugated to AlexaFluor488 | Prostate cancer | Binding (antibody) |
| Zevalin | Ibritumomab tiuxetan | Non-Hodgkin's lymphoma | Binding (antibody) |
| BODIPY-FL-Cetuximab | BODIPY-FL-neutravidin-biotin-Cetuximab BODIPY-FL-Cetuximab | Epidermoid tumors (Epidermal growth factor, HER1 receptor) | Binding (antibody) |
| Trast-RhodG | Trastuzumab-rhodamine greenTrast-RhodG | Breast cancer | Binding (antibody) |
| Bexxar | Tositumomab | Non-Hodgkin's lymphoma | Binding (antibody) |

APPENDIX-continued

EXEMPLARY FLUOROPHORES, EMITTERS, TRACERS, ETC.

| | | | |
|---|---|---|---|
| Db-18-Rluc8 | T84.66 Anti-CEA diabody-GSTSGSGKPGSGEGSTSG-*Renilla* luciferaseDb-18-Rluc8 | Colorectal Cancer | Binding (antibody) |
| Herceptin | trastuzumab | Breast cancer | Binding (antibody) |
| Avastin | bevacizumab | Colorectal Cancer | Binding (antibody) |
| Tarceva | erlotinib | Lung cancer | Binding (antibody) |
| Rituxan | rituximab | Non-Hodgkin's lymphoma | Binding (antibody) |
| QT, QD-T | Quantum dot-trastuzumabQT | Breast cancer | Binding (antibody) |
| Invitrogen antibodies | | cancers, various | Binding (antibody) |
| Cetuximab-Cy5.5 | Cy5.5 conjugated anti-epidermal growth factor receptor monoclonal antibody Cetuximab-Cy5.5 | Prostate cancer | Binding (antibody) |
| Alexa680-Bevacizumab | Alexa Fluor 680-BevacizumabAlexa Fluor 680-Bevacizumab | Pancreatic cancer | Binding (antibody) |
| VCAM-NP | Anti-vascular cell adhesion molecule monoclonal antibody M/K-2.7 conjugated cross-linked iron oxide-Cy5.5 nanoparticles VCAM-NP | atherosclerosis | Binding (antibody) |
| F19 (BIBH-1) | | Colorectal Cancer | Binding (antibody) |
| Anti-ICAM ACPLs | Anti-ICAM-1 antibody-conjugated paramagnetic liposomesAnti-ICAM ACPLs | multiple sclerosis | Binding (antibody) |
| Cy5.5- Trastuzumab | Cy5.5-Trastuzumab | Breast cancer | Binding (antibody) |
| QD-PMSA Ab J591 | Quantum dot-prostate-specific membrane antigen antibody J591 QD-PSMA Ab J591 | Prostate cancer | Binding (antibody) |
| MGITC-AuNPs-scFvB10 | Malachite green-isothiocyanate-polyethylene glycol-gold nanoparticles conjugated with scFv anti-EGFR B10 antibodyMGITC-AuNPs-scFvB10 | Breast cancer | Binding (antibody) |
| Erbitux | Cetuximab | Prostate cancer | Binding (antibody) |
| Cy5.5-GHPGGPQK(Fitc)C-PL-MPEG, Cy5.5-CatK-PGC | Cy5.5-Gly-His-Pro-Gly-Gly-Pro-Gln-Gly-Lys(Fitc)-Cys-Poly-L-lysine-methoxypolyethylene glycol Cy5.5-GHPGGPQK(Fitc)C-PL-MPEG | atherosclerosis | Binding (Enzyme) |
| Cy5.5-PL-MPEG | Cy5.5-Poly-L-lysine-methoxypolyethylene glycolCy5.5-PL-MPEG | cancers, various | Binding (Enzyme) |
| IPL-NP | IPLVVPLGGSC(Cy5.5-Cross-linked iron oxide)K(Fitc) IPL-NP | Prostate cancer | Binding (Enzyme) |
| Cy5.5-GGPRQITAGK(Fitc)C-PL-MPEG | Cy5r5-GGPRQITAGK(Fitc)C-Poly-L-lysine-methoxypolyethylene glycolCy5.5-GGPRQITAGK(Fitc)C-PL-MPEG | myocardial infarction Gelatinase | Binding (Enzyme) |
| CNA35-OG488 | Collagen -binding adhesion protein 35-Oregon Green 488 CNA35-OG488 | atherosclerosis | Binding (protein) |
| NIAD-4 | [[5'-(4-Hydroxyphenyl)[2,2'-bithiophen]-5-yl]methylene]-propanedinitrile NIAD-4 | Alzheimer's disease | Binding (protein) |
| QD-Apt(Dox) | Quantum dot-A10 RNA aptamer-doxorubicin conjugate QD-Apt(Dox) | Prostate cancer | Binding (PSMA) |
| TCL-SPION-Apt(Dox) | Thermally cross-linked superparamagnetic iron oxide nanoparticle-A10 RNA aptamer-doxorubicin conjugateTCL-SPION-Apt(Dox) | Prostate cancer | Binding (PSMA) |
| GPI-78 | GPI-78 | Prostate cancer | Binding (PSMA) |
| VINP-28 NP | VCAM-1 internalizing peptide-28 nanoparticles VINP-28 NP | atherosclerosis | Binding (Receptor) |
| Tf$^{NIR}$-Lip$^{NBD}$-CA complex | Alexa Fluor 680-labeled transferrin-cationic (NBD-labeled DOPE-DOTAP) liposome-encapsulated gadopentetate dimeglumine complex TfNIR-LipNBD-CA complex | Breast cancer | Binding (Receptor) |
| Alexa Fluor 680-G-G-G-BN[7-14]NH$_2$ | Alexa Fluor 680-glycylglycylglycine-bombesin[7-14]NH2 peptideAlexa Fluor 680-G-G-G-BN[7-14]NH2 | Breast cancer | Binding (Receptor) |
| Cy5-RAFT-c(-RGDfK-)$_4$ | Cy5 -Regioselectively addressable functionalized template-[cyclo-(RGD-d-Phe-Lys)]4 peptide Cy5-RAFT-c(-RGDfK-)4 | Ovarian cancer | Binding (Receptor) |
| RAFT-c(-RGDfK-)$_4$-Cy5-SS-Q | Self-quenched-regioselectively addressable functionalized template-[cyclo-(RGD-d-Phe-Lys)]4 peptide-Cy5-fluorescence quencher QSY21RAFT-c(-RGDfK-)4-Cy5-SS-Q | melanoma | Binding (Receptor) |
| $^{64}$Cu-DOTA-QD-RGD, $^{64}$Cu-DOTA-QD-c(RGDyK) | 64Cu-Tetraazacyclododecane-N',N",N"'-tetraacetic acid-quantum dot-c(Arg-Gly-Asp-D-Tyr-Lys)64Cu-DOTA-QD-c(RGDyK) | glioblastoma | Binding (Receptor) |
| NIR2-Folate | NIR2-Folate | Ovarian cancer | Binding (Receptor) |
| PTP-CLIO-Cy5.5 | Lys-Thr-Leu-Leu-Pro-Thr-Pro-cross-linked iron oxide-Cy5.5PTP-CLIO-Cy5.5 | Pancreatic cancer | Binding (Receptor) |
| BN-CLIO-Cy5.5 | Bombesin peptide conjugated-cross-linked iron oxide Cy5.5 BN-CLIO-Cy5.5 | Pancreatic cancer | Binding (Receptor) |
| IRDye 800CW-EGF | IRDye 800CW-Epidermal growth factorIRDye 800CW-EGF | Prostate cancer | Binding (Receptor) |
| GmSA-20ROX | Galactosamine-serum albumin-rhodamineX20GmSA-20ROX | Ovarian cancer | Binding (Receptor) |
| Cy5.5-Endostatin | Cy5.5-Endostatin | angiogenesis (tumor) | Binding (Receptor) |
| GSA-RhodG | Galactosyl serum albumin-rhodamine greenGSA-RhodG | Ovarian cancer | Binding (Receptor) |

APPENDIX-continued

EXEMPLARY FLUOROPHORES, EMITTERS, TRACERS, ETC.

| | | | |
|---|---|---|---|
| Cy5.5-scVEGF$_{121}$ | Cy5.5-Single-chain Cys-tagged vascular endothelial growth factor-121Cy5.5-scVEGF121 | Breast cancer | Binding (Receptor) |
| QD705-RGD | Arginine-glycine-aspartic acid peptide-labeled quantum dot 705QD705-RGD | angiogenesis (tumor) | Binding (Receptor) |
| $^{111}$In-DLIA-IL11α | 111In-DTPA-Bz-NH-SA-K(IR-783-S—Ph—CO)-c(CGRRAGGSC)NH2111In-DLIA-IL11Rα | angiogenesis (tumor) | Binding (Receptor) |
| Cy5.5-EGF | Cy5.5-Epidermal growth factor Cy5.5-EGF | Breast cancer | Binding (Receptor) |
| OA02-Cy5.5 | D-Cys-D-Asp-Gly-HCit-Gly-Pro-Gln-D-Cys-Ebes-Ebes-Lys-Cy5.5 OA02-Cy5.5 | Ovarian cancer | Binding (Receptor) |
| RGD-Cy5.5 | Cyclo(RGDyK)-Cy5.5 RGD-Cy5.5 | angiogenesis (tumor) | Binding (Receptor) |
| AdTSTA-FL | Ad5-(PSE-BC)-(GAL4-(VP16)2)-(GAL4)5-Fluc AdTSTA-FL | Prostate cancer | Binding (Receptor) |
| $^{177}$Lu-LS172 | 177Lu-DOTA-Tyr3-c(Cys-Tyr-Trp-Lys-Thr-Cys)-Thr-Lys(cypate)-NH2177Lu-LS172 | Lung cancer | Binding (Receptor) |
| $^{64}$Cu-LS172 | 64Cu-DOTA-Tyr3-c(Cys-Tyr-Trp-Lys-Thr-Cys)-Thr-Lys(cypate)-NH264Cu-LS172 | Lung cancer | Binding (Receptor) |
| Cyp-GRD, Cyp-GRDSPK | Cypate-Gly-Arg-Asp-Ser-Pro-Lys Cyp-GRD | Lung cancer | Binding (Receptor) |
| LLP2A-SA-Alexa680 | LLP2A-biotin-streptavidin-Alexa Fluor 680 LLP2A-SA-Alexa680 | lymphoid tumor | Binding (Receptor) |
| RGD-PEG-SWNTs | Cyclic Arg-Gly-Asp-polyethyleneglycol-single-walled carbon nanotubes RGD-PEG-SWNTs | osteosarcomas | Binding (Receptor) |
| Cy7-E{E[c(RGDyK)]$_2$}$_2$ | Cy7-Tetrameric arginine-glycine-aspartic acid peptide Cy7-E{E[c(RGDyK)]2}2 | angiogenesis (tumor) | Binding (Receptor) |
| $^{111}$In-DTPA-Bz-SA-Lys-IRDye800-c(RGDfK) | 111In-Diethylenetriaminepentaacetic acid-benzyl-succinamido-Lys-IRDye800-c(Arg-Gly-Asp-D-Phe-Lys)111In-DTPA-Bz-SA-Lys-IRDye800-c(RGDfK) | angiogenesis (tumor) | Binding (Receptor) |
| FITC-IAC | 4-[2-(3,4,5,6-Tetrahydropyrimidin-2-ylamino)ethyloxy]benzoyl-2-(S)-[N-3-amino-neopenta-1-carbamyl)]-aminoethylsulfonylamino-β-alanine fluorescein thiourea FITC-IAC | angiogenesis (tumor) | Binding (Receptor) |
| $^{64}$Cu-DOTA-QD-VEGF, $^{64}$Cu-DOTA-QD-VEGF$_{121}$ | 64Cu-1,4,7,10-Tetraazacyclododecane-1,4,7,10-tetraacetic acid-quantum dot-vascular endothelial growth factor 64Cu-DOTA-QD-VEGF | angiogenesis (tumor) | Binding (Receptor) |
| Cy5.5-Tat-T cells | Cy5.5-CGRRRQRRKKRG-Labeled T lymphocytes Cy5.5-Tat-T cells | multiple sclerosis | cell migration |
| X-sight LSS dyes | | Non specific | Dye |
| Cresyl Violet | cresyl violet acetate | nerve IDs | Dye |
| "DiI" Carbocyanine | 1,1'-dioctadecyl-3,3,3',3'-tetramethylindocarbocyanine perchlorate ('DiI'; DiIC18(3)), | nerve IDs | dye |
| "DiA" Carbocyanine | | nerve IDs | dye |
| X-Sight Nanospheres | | Non specific | Dye |
| Pam78 | Pamidronate-IRDye78 Pam78 | skeletal changes | Dye |
| ICG | Indocyanine Green | lymphatics, vasculature | Dye |
| Fluroscein | | cancers, various | Dye |
| AngioSense | | vasculature | Large particle |
| HSA800 | IRDye 800CW-Human serum albuminHSA800 | cancers, various | Lymph node trapping |
| IR-786 | IR-786 perchlorate IR-786 | bladder carcinoma | Membrane potential and ionic |
| microbubble | | vasculature | Microbubble |
| AngioSPARK | | vasculature | Nanoparticle |
| Au-PEG-nanoshells | Gold-polyethylene glycol nanoshellsAu-PEG-nanoshells | Colorectal Cancer | Phagocytosis |
| $^{64}$Cu-TNP | 64Cu-DTPA-CLIO-VT680 64Cu-TNP | atherosclerosis | Phagocytosis |
| ProSense | | cancers, various | Proteolytic cleavage |
| Cy5.5-R4-SC-CLIO | Cy5.5-Arg-Arg-Arg-Arg-crosslinked iron oxide nanoparticle Cy5.5-R4-SC-CLIO | cancers, various | Proteolytic cleavage |
| GB137 | Cbz-Phe-Lys(Cy5)-methyl ketone-2,6,dimethylterephthalic amide-hexyl-QSY 21GB137 | cancers, various | Proteolytic cleavage |
| MMP Sense | | cancers, various | Proteolytic cleavage |
| T$_{CAP}$Q$_{647}$ | Ac-rkkrrorrrGK(QSY21)DEVDAPC(Alexa Fluor 647)-NH2TCAPQ647 | apoptosis | Proteolytic cleavage |
| IR-2 | IR-783-GlucosamineIR-2 | cancers, various | Tumor uptake |
| CLIO-Cy5.5 | Cross-linked iron oxide-Cy5.5CLIO-Cy5.5 | glioblastoma | Tumor uptake |
| siGFP-CLIO-Cy5.5 | Green fluorescent protein specified small interfering RNA-cross-linked iron oxide nanoparticles-Cy5.5 siGFP-CLIO-Cy5.5 | cancers, various | Tumor uptake |
| siSurvivin-CLIO-Cy5.5 | Survivin specified small interfering RNA-CLIO-Cy5.5 siSurvivin-CLIO-Cy5.5 | cancers, various | Tumor uptake |
| 5-ALA | 5-aminolevulinic acid converted in vivo to protoporphyrin IX | Prostate cancer | Tumor uptake |
| HSV | Herpes Simplex virus | nerve IDs | |

APPENDIX-continued

EXEMPLARY FLUOROPHORES, EMITTERS, TRACERS, ETC.

| Agent Name | Detection Methodology | Fluorescence Range | color | Notes |
|---|---|---|---|---|
| EF5 | histology | n/a | | Cancer hypoxia |
| Superhance | optical | 680/700 | NIR | 2 h half life in plasma vasculature (albumin binding) |
| A15 | optical | NIR | NIR | acute thrombi, Activated coagulation factor XIIIa (FXIIIa) |
| AnxA5-QD-Gd | optical | NIR | NIR | Apoptosis |
| CREKA-SPIO-Cy7 | optical | 740-760/770-790 | NIR | breast cancer, Clotted plasma proteins |
| pLux-expressing *E. coli* | optical | NIR | NIR | *e coli* migrate to tumors, breast cancer, Non-specific tumor |
| AnxCLIO-Cy5.5 | optical | 675/694 | red | descending coronary artery, Phosphatidylserine |
| Cy5.5-Annexin V | optical | 675/694 | red | lung carcinoma, Phosphatidylserine |
| CLIO-EPPT | optical | 675/694 | red | pancreatic cancer, Tumor antigen |
| AOI987 | optical | ? | | Alzheimer's disease, Aggregates of β-amyloid (Aβ) peptides |
| OsteoSense | optical | 680/700 and 750/780 | NIR | hydroxyapatite (skeletal changes) |
| Qsmart | optical | ? | | apoptosis |
| IntegriSense | optical | 680/700 | NIR | integrin (angiogenesis and tumor metastasis) |
| Cy7-DPA-Zn | optical | NIR | NIR | leg infection, Phosphatidylglycerol and phosphates (anionic surface of bacteria) |
| SIDAG | optical | 800/830 | NIR | tumors, Non-targeted |
| Vectibix | none | n/a | | Colorectal Cancer (EGFR binder) |
| MDX1201 A488 | optical | 488/530 | green | Prostate Cancer Can manufacture their antibody in house for clinical trial |
| Zevalin | none | n/a | | Non-Hodgkin lymphoma (CD20) |
| BODIPY-FL-Cetuximab | optical | 505/513 | green | FDA approved antibody, Epidermoid tumors (Epidermal growth factor, HER1 receptor) |
| Trast-RhodG | optical | 502/527 | green | FDA approved antibody, Epidermal growth factor, EGF HER2 receptor |
| Bexxar | none | n/a | | Non-Hodgkin lymphoma (CD20) |
| Db-18-Rluc8 | optical | 535/550 | green | common tumors, Carcinoembryonic antigen (CEA) |
| Herceptin | none | n/a | | Breast/ovarian cancer (HER-2 binding) |
| Avastin | none | n/a | | Colon, rectum, lung, breast cancer (VegF binder) |
| Tarceva | none | n/a | | Lung cancer (HER1/EGFR inhibitor) |
| Rituxan | none | n/a | | Non Hodgkin's lymphoma (anti CD20 antibody) |
| QT, QD-T | optical | 675/694 | red | FDA approved antibody, breast cancer, EGF HER2 receptor |
| Invitrogen antibodies | optical | multiple | | Can custom manufacture an antibody to any target protein |
| Cetuximab-Cy5.5 | optical | 675/694 | red | FDA approved antibody, cell carcinoma, Epidermal growth factor receptor |

APPENDIX-continued

EXEMPLARY FLUOROPHORES, EMITTERS, TRACERS, ETC.

| | | | | |
|---|---|---|---|---|
| Alexa680-Bevacizumab | optical | 684/707 | NIR | FDA approved antibody, pancreatic tumors, Vascular endothelial growth factor (VEGF) |
| VCAM-NP | optical | 675/694 | red | Bacterial lipopoly-saccharide, Vascular cell adhesion molecule-1 (VCAM-1) |
| F19 (BIBH-1) | histology | n/a | | Colon Cancer |
| Anti-ICAM ACPLs | optical | 590/620 | orange | multiple sclerosis, ICAM-1 |
| Cy5.5- Trastuzumab | optical | 675/694 | red | FDA approved antibody, tumor cells, Human epidermal growth factor receptor 2 (HER2) |
| QD-PMSA Ab J591 | optical | NIR | NIR | Prostate cancer |
| MGITC-AuNPs-scFvB10 | optical | NIR | NIR | tumor tissue, EGFR, HER1 |
| Erbitux | none | n/a | | Prostate Cancer |
| Cy5.5-GHPGGPQK(Fitc)C-PL-MPEG, Cy5.5-CatK-PGC | optical | 675/694 | red | atherosclerosis |
| Cy5.5-PL-MPEG | optical | 675/694 | red | Cathepsin protease activity (cancer, arthritis, athero-sclerosis, angiogenesis) |
| IPL-NP | optical | 675/694 | red | LNCaP tumor, Hepsin |
| Cy5.5-GGPRQITAGK(Fitc)C-PL-MPEG | optical | 675/694 | red | myocardial infarction Gelatinases (MMP-2 and MMP-9) |
| CNA35-OG488 | optical | 496/510-524 | green | atherosclerosis |
| NIAD-4 | optical | 625/ | red | Amyloid - B (alzheimer's) |
| QD-Apt(Dox) | optical | 550/650 | red | prostate cancer (PSMA) |
| TCL-SPION-Apt(Dox) | optical | NIR | NIR | prostate cancer (PSMA) |
| GPI-78 | optical | 772/790 | NIR | prostate cancer, Prostate-specific membrane antigen (PSMA), or N-acetyl α-linked acidic dipeptidase (NAALADase) |
| VINP-28 NP | optical | 675/694 | red | Vascular cell adhesion molecule-1 (VCAM-1) |
| $Tf^{NIR}$-$Lip^{NBD}$-CA complex | optical | 679/720 | NIR | breast cancer, Transferrin receptor (TfR) |
| Alexa Fluor 680-G-G-G-BN[7-14]$NH_2$ | optical | 679/720 | NIR | breast tumors, Gastrin-releasing peptide receptor (GRP-R) |
| Cy5-RAFT-c(-RGDfK-)$_4$ | optical | 649/670 | red | ovarian cancer, Integrin $\alpha_v\beta_3$ |
| RAFT-c(-RGDfK-)$_4$-Cy5-SS-Q | optical | 649/670 | red | skin tumor, Integrin $\alpha_v\beta_3$ |
| $^{64}$Cu-DOTA-QD-RGD, $^{64}$Cu-DOTA-QD-c(RGDyK) | optical | NIR | NIR | coronary angiogenesis, Integrin $\alpha_v\beta_3$ |
| NIR2-Folate | optical | 665/686 | red | ovarian Cancer, intestinal adenoma, arthritis |
| PTP-CLIO-Cy5.5 | optical | 675/694 | red | pancreatic cancer Plectin-1 |
| BN-CLIO-Cy5.5 | optical | 675/694 | red | pancreatic ductal adenocarcinoma, Bombesin receptor |
| IRDye 800CW-EGF | optical | 675/694 | red | Metastatic Prostate Cancer EGF receptor (EGFR, HER1) |
| GmSA-20ROX | optical | 595/610 | orange | ovarian adenocarcinomas, β-d-galactose receptor |
| Cy5.5-Endostatin | optical | 675/694 | red | Tumor angiogenesis, Putative endostatin receptor |
| GSA-RhodG | optical | 502/527 | green | Ovarian Cancer |
| Cy5.5-scVEGF$_{121}$ | optical | 675/694 | red | mammary adenocarcinoma tumors, VEGF receptors |
| QD705-RGD | optical | 705/ | NIR | Integrin (angiogenesis and tumor metastasis) |
| $^{111}$In-DLIA-IL11α | optical | NIR | NIR | Interleukin-11 (IL- 11) receptor αvβ3 integrin is the most prominent receptor affecting tumor growth, tumor invasiveness, metastasis, tumor-induced angiogenesis, |

APPENDIX-continued

EXEMPLARY FLUOROPHORES, EMITTERS, TRACERS, ETC.

| | | | | |
|---|---|---|---|---|
| Cy5.5-EGF | optical | 675/694 | red | inflammation, osteoporosis, and rheumatoid arthritis EGF receptor (EGFR HER1) |
| OA02-Cy5.5 | optical | 675/694 | red | Integrin a3B1 (Ovarian cancer) |
| RGD-Cy5.5 | optical | 675/694 | red | various tumors, Integrin $\alpha_v\beta_3$ |
| AdTSTA-FL | optical | 560/ | yellow/green | Adenovirus, Prostate cancer, breast cancer w/Androgen receptor |
| $^{177}$Lu-LS172 | optical | NIR | NIR | lung adenocarcinoma Somatostatin receptor subtype-2 (SSTR-2) |
| $^{64}$Cu-LS172 | optical | 700/900 | NIR | lung adenocarcinoma, Somatostatin receptor subtype-2 (SSTR-2) |
| Cyp-GRD, Cyp-GRDSPK | optical | 778/805 | NIR | lung carcinomas, $\alpha_v\beta_3$ integrin |
| LLP2A-SA-Alexa680 | optical | 684/707 | NIR | lymphoid tumor cells, Integrin $\alpha_4\beta_1$ |
| RGD-PEG-SWNTs | optical | NIR | NIR | osteosarcomas, neuroblastomas, glioblastomas, invasive melanomas, & carcinomas, Integrin $\alpha_v\beta_3$ |
| Cy7-E{E[c(RGDyK)]$_2$}$_2$ | optical | 743/767 | NIR | tumor vasculature, Integrin $\alpha_v\beta_3$ |
| $^{111}$In-DTPA-Bz-SA-Lys-IRDye800-c(RGDfK) | optical | NIR | NIR | tumor, Integrin $\alpha_v\beta_3$ |
| FITC-IAC | optical | 675/694 | red | tumor accumulation, Integrin $\alpha_v\beta_3$ integrin-targeted molecular imaging agent conjugated with fluorescein isothiocyanate (FITC) that was developed for fluorescence imaging of tumor vasculature angiogenesis |
| $^{64}$Cu-DOTA-QD-VEGF, $^{64}$Cu-DOTA-QD-VEGF$_{121}$ | optical | NIR | NIR | Vascular endothelial growth factor receptor 2 (VEGFR-2) |
| Cy5.5-Tat-T cells | optical | 675/694 | red | neurological impairment, Inflamed tissue |
| X-sight LSS dyes | optical | 635/733 669/755 | NIR | can be conjugated to any agents |
| Cresyl Violet | confocal | 488/? | qreen | No drug company sponsorship, as old dye, off any patents nerve IDs |
| "DiI" Carbocyanine | optical | 630? | red/orange | Red-orange-fluorescent lipophilic probe; widely used as a neuronal tracer, proposed by Tewari on gold particles |
| "DiA" Carbocyanine | optical | 560/ | yellow/green | yellow green-fluorescent lipophilic probe; used as a neuronal tracer |
| X-Sight Nanospheres | optical | 549/569 650/673 | 691/75 761/7 | can be conjugated to any agents |
| Pam78 | optical | 806/771 | NIR | hydroxyapatite (skeletal changes) |
| ICG | optical | 810/830 | NIR | lymphatics, vasculature |
| Fluroscein | confocal | 488/520 | green | Optiscan and Cellvizio both use Fluroscein, cellular substructures |
| AngioSense | optical | 680/700 and 750/780 | NIR | Have long duration in the vasculature (12+ hours) because of large size | vasculature |
| HSA800 | optical | NIR | NIR | metastasis, Non-targeted |
| IR-786 | optical | 795-815 | NIR | Commercially available, bladder carcinoma, Mitochondria and endoplasmic reticulum cancer vascularity |
| microbubble | ultrasound | na | | |
| AngioSPARK | optical | 680/700 and 750/780 | NIR | Extremely long duration (40+ hours) in vasculature |
| Au-PEG-nanoshells | optical | NIR | NIR | colon carcinoma tumors, Phagocytes and tumor cells |
| $^{64}$Cu-TNP | optical | 670/688 | red | Macrophages |
| ProSense | optical | 680/700 and 750/780 | NIR | Cathepsin protease activity (cancer, arthritis, atherosclerosis, angiogenesis) |
| Cy5.5-R4-SC-CLIO | optical | 675/694 | red | Proteases cleaving Cathepsin B as imaging agent, differentially |

APPENDIX-continued

EXEMPLARY FLUOROPHORES, EMITTERS, TRACERS, ETC.

| | | | | | expressed in tumor and healthy tissue | |
|---|---|---|---|---|---|---|
| GB137 | optical | 646/664 | red | breast cancer, glioblastoma, arthritis, Cysteine cathepsin | |
| MMP Sense | optical | 680/700 | NIR | Metalloproteinase activity (cancer metastasis, rheumatoid arthritis) | |
| $T_{CAP}Q_{647}$ | optical | 650/665 | red | apoptosis | |
| IR-2 | optical | 750/ | NIR | cancer Lysosomes | |
| CLIO-Cy5.5 | optical | 675/694 | red | brain tumor, Phagocyte and tumor cell | |
| siGFP-CLIO-Cy5.5 | optical | 675/694 | red | Tumors | |
| siSurvivin-CLIO-Cy5.5 | optical | 675/694 | red | Tumors | |
| 5-ALA | optical | 380-420/"red" | red | Based on an FDA approved photodynamic Therapy drug | Prostate cancer, Glioma |
| HSV | optical | NIR | NIR | Being researched by Novadaq partners, inactivated HSV travels retrograde up nerve fibers | |

What is claimed is:

1. A method comprising:
desaturating, by a processor in a surgical system, a visible color image of tissue into a desaturated image, the visible color image being a reflected white light image captured from visible electro-magnetic spectrum light, the visible electro-magnetic spectrum light being from a surgical site in a patient;
coloring, by the processor, an enhanced image representing data captured from the surgical site with a visible color to form a color enhanced image, the data being captured from light outside the visible electro-magnetic spectrum;
superimposing, by the processor, the color enhanced image and the desaturated image together to form a blended image of the surgical site for display on a display device.

2. The method of claim 1, further comprising:
illuminating the surgical site the patient with visible light in the visible electro-magnetic spectrum;
capturing the visible color image of the surgical site in the patient; and
capturing the data from light from a biomarker in the surgical site.

3. The method of claim 2, further comprising:
prior to the capturing the data, exposing the surgical site in the patient to electro-magnetic radiation outside the visible electro-magnetic spectrum to excite the biomarker.

4. The method of claim 3, wherein the biomarker comprises indocyanine green; and wherein the electro-magnetic radiation outside the visible electro-magnetic spectrum is near-infrared radiation.

5. The method of claim 1, further comprising:
prior to the superimposing, setting a first relative brightness between the color enhanced image and the desaturated image.

6. The method of claim 5, wherein
the first relative brightness is a predetermined brightness level, and
the desaturation of the visible color image is at a predetermined level of desaturation.

7. The method of claim 5, further comprising:
receiving an input from a user interface, the input indicating to vary the setting of the relative brightness between the color enhanced image and the desaturated image to a second relative brightness.

8. The method of claim 5, further comprising:
receiving an input from a user interface, the input indicating to vary the level of desaturation to desaturate the visible color image of the surgical site.

9. The method of claim 8, the input indicating to fully desaturate the visible color image of the surgical site, and thereby the desaturated image is a black and white image.

10. The method of claim 1, wherein the enhanced image is one of a near-infra-red fluorescence image, visible light fluorescence image, or a raster scan of spectral characteristics of the surgical site including clinical information with spatial variation.

11. The method of claim 1, wherein the enhanced image is formed of point measurements of a measureable tissue parameter.

12. The method of claim 11, wherein the measureable tissue parameter is tissue impedance, point detection of cancer cells, or point detection of a predetermined cell type.

13. The method of claim 1, further comprising temporally registering and spatially registering the color enhanced image with the desaturated image, prior to the superimposing.

14. An apparatus comprising:
an image processor, the image processor being configured to desaturate a captured visible color image into a desaturated image, the visible color image being a reflected white light image captured from visible electro-magnetic spectrum light, the visible electro-magnetic spectrum light being from a surgical site in a patient, the image processor being configured to color a first enhanced image representing first captured data with a first visible color to form a first enhanced color image, the first captured data being first data from the surgical site, and the first data being outside the visible electro-magnetic spectrum; and
a display device coupled to the image processor, the display device being configured to display a superpostion of the desaturated image and the color enhanced image together to form a blended image of the surgical site.

15. The apparatus of claim 14,
the image processor further being configured to color a second enhanced image representing second captured data with a second visible color to form a second enhanced color image, the second captured data being second data captured from the surgical site, the second data being outside the visible electro-magnetic spectrum, the first data being different from the second data, and the first color being different from the second color; and the display device further being configured to display a superimposition of the desaturated image, the first color enhanced image, and the second color enhanced image together to form the blended image of the surgical site.

16. The apparatus of claim 14, further comprising:
a user interface including a user selectable device to adjust the relative brightness between the desaturated image and the first color enhanced image displayed on the display device.

17. The apparatus of claim 15, further comprising:
a user interface including a first user selectable device to adjust the brightness of the desaturated image displayed on the display device and a second user selectable device to adjust the brightness of the second color enhanced image displayed on the display device.

18. The apparatus of claim 14, wherein
a camera unit coupled to the image processor, the camera unit comprising;
 a first sensor sensitive to ranges of wavelengths in the visible electromagnetic spectrum; and
 a second sensor sensitive to ranges of wavelengths outside the visible electromagnetic spectrum.

19. The apparatus of claim 14, wherein
a portion of the desaturated image includes a desaturated image of surgical tools.

20. The apparatus of claim 14, further comprising an illumination source configured to provide illumination that excites a biomarker in the surgical site wherein the first data is from the excited biomarker.

21. The apparatus of claim 20, wherein the biomarker comprises indocyanine green (ICG).

22. The apparatus of claim 14, wherein the first captured data is data captured from an X-ray of bone tissue under surface tissue.

23. A machine readable media have stored thereon instructions that when executed by a machine causes the machine to perform operations comprising:
 reducing color in color images to form desaturated images, the color images being of tissue in a surgical site in a patient, and the color images being reflected white light images in the visible electro-magnetic spectrum;
 making non-visible tissue feature images into color enhanced images, the tissue feature being in the surgical site; and
 superimposing the color enhanced images and the desaturated images together to form blended images for display on at least one display device.

24. The machine readable media of claim 23, wherein the non-visible tissue feature images comprise images captured from light outside the visible electro-magnetic (EM) spectrum.

25. The machine readable media of claim 23, wherein
the non-visible characteristic tissue features of the surgical site are made visible over the tissue captured in desaturated images by a false color.

26. A method comprising:
 capturing a visible color image of a surgical site illuminated by visible light, the visible color image being a reflected white light image captured from visible electro-magnetic spectrum light;
 desaturating the visible color image of the surgical site into a visible gray image;
 capturing a fluorescent image of fluorescing tissue in the surgical site, wherein the fluorescing tissue appears in a visible color; and
 generating a displayable image comprising a superimposition of the visible fluorescent image and the visible gray image together to form a blended image of the surgical site.

27. The method of claim 26, wherein the desaturating comprises:
 substantially removing all color from the visible color image to form the visible gray image.

28. The method of claim 26, wherein the obtaining of the fluorescent image comprises:
 exposing the surgical site to electromagnetic radiation outside the visible electromagnetic spectrum.

29. The method of claim 26, further comprising:
 coloring the fluorescing tissue in the fluorescent image with the visible color.

30. The method of claim 26, further comprising:
 displaying the displayable image on a display device; and
 adjusting a level of brightness of one or both of the visible gray image and the fluorescent image.

31. The method of claim 26, further comprising:
 displaying the displayable image on a display device; and
 adjusting a level of desaturation of the visible color image.

* * * * *